(12) United States Patent
Ando et al.

(10) Patent No.: US 8,569,253 B2
(45) Date of Patent: *Oct. 29, 2013

(54) METHODS AND COMPOSITIONS FOR GENE INACTIVATION

(75) Inventors: Dale Ando, Walnut Creek, CA (US);
Michael C. Holmes, Oakland, CA (US);
Gary Ka Leong Lee, San Leandro, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 184 days.

This patent is subject to a terminal disclaimer.

(21) Appl. No.: 13/068,348

(22) Filed: May 9, 2011

(65) Prior Publication Data

US 2012/0309091 A1    Dec. 6, 2012

Related U.S. Application Data

(63) Continuation of application No. 11/805,707, filed on May 23, 2007, now Pat. No. 7,951,925.

(60) Provisional application No. 60/808,501, filed on May 25, 2006, provisional application No. 60/847,269, filed on Sep. 26, 2006, provisional application No. 60/926,911, filed on Apr. 30, 2007.

(51) Int. Cl.
*A61K 48/00* (2006.01)
*A61K 38/00* (2006.01)
*C07H 21/02* (2006.01)
*C12N 15/00* (2006.01)
*A01N 63/00* (2006.01)

(52) U.S. Cl.
USPC ..... 514/44 R; 530/300; 536/23.1; 435/320.1; 424/93.21

(58) Field of Classification Search
None
See application file for complete search history.

(56) References Cited

U.S. PATENT DOCUMENTS

| | | |
|---|---|---|
| 5,176,996 A | 1/1993 | Hogan et al. |
| 5,356,802 A | 10/1994 | Chandrasegaran |
| 5,420,032 A | 5/1995 | Marshall |
| 5,422,251 A | 6/1995 | Fresco |
| 5,436,150 A | 7/1995 | Chandrasegaran |
| 5,487,994 A | 1/1996 | Chandrasegaran |
| 5,585,245 A | 12/1996 | Johnsson et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,453,242 B1 | 9/2002 | Eisenberg et al. |
| 6,503,717 B2 | 1/2003 | Case et al. |
| 6,534,261 B1 | 3/2003 | Cox et al. |
| 6,599,692 B1 | 7/2003 | Case et al. |
| 6,607,882 B1 | 8/2003 | Cox, III et al. |
| 6,689,558 B2 | 2/2004 | Case |
| 6,787,316 B2 | 9/2004 | Stewart et al. |
| 6,824,978 B1 | 11/2004 | Cox, III et al. |
| 6,833,252 B1 | 12/2004 | Dujon et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,163,824 B2 | 1/2007 | Cox, III et al. |
| 7,951,925 B2 * | 5/2011 | Ando et al. ........... 536/23.1 |
| 2003/0232410 A1 | 12/2003 | Liljedahl et al. |
| 2003/0233672 A1 | 12/2003 | Li et al. |
| 2005/0026157 A1 | 2/2005 | Baltimore |
| 2005/0064474 A1 | 3/2005 | Urnov et al. |
| 2005/0208489 A1 | 9/2005 | Carroll |
| 2006/0188987 A1 | 8/2006 | Guschan et al. |
| 2007/0134796 A1 | 6/2007 | Holmes et al. |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/44350 A1 | 10/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |

(Continued)

OTHER PUBLICATIONS

Alkhatb, "CC CKR5: A Rantes, MIP-16, MIP-1β Receptor as a Fusion Cofactor for Macrophage-Tropic HIC-1," *Science* 272:1955-1958 (1996).

Alvarez, et al. "A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," *Hum. Gene Ther.* 8(5):597-613 (1997).

Argast, et al., "I-PPOI and ICREI Homing Site Sequence Degeneracy Determined by Random Mutagenesis and Sequenctial In Vitro Enrichment," *J. Mol. Biol.* 280:345-353 (1988).

Arnould, et al., "Engineering of Large Numbers of Highly Specific Homing Endonucleases That Induce Recombination on Novel DNA Targets," *J Mol Biol* 355:443-458 (2006).

Ashworth, et al., "Computational Redesign of Endonuclease DNA Binding and Cleavage Specificity," *Nature* 442:656-659 (2006).

Beerli, et al., "Engineering Polydactyl Zinc-Finger Transcription Factors," *Nature Biotechnology* 20:135-141 (2002).

(Continued)

*Primary Examiner* — Janice Li
(74) *Attorney, Agent, or Firm* — Pasternak Patent Law; Dahna S. Pasternak

(57) ABSTRACT

Disclosed herein are methods and compositions for inactivating CCR-5 genes, using zinc finger nucleases (ZFNs) comprising a zinc finger protein and a cleavage domain or cleavage half-domain. Polynucleotides encoding ZFNs, vectors comprising polynucleotides encoding ZFNs, such as adenovirus (Ad) vectors, and cells comprising polynucleotides encoding ZFNs and/or cells comprising ZFNs are also provided.

23 Claims, 17 Drawing Sheets

(56) References Cited

FOREIGN PATENT DOCUMENTS

| WO | WO 02/057308 A2 | 7/2002 |
| WO | WO 02/099084 A2 | 12/2002 |
| WO | WO 03/016496 A2 | 2/2003 |
| WO | WO 2007/014275 A2 | 1/2007 |

OTHER PUBLICATIONS

Benkirane, et al., "Mechanism of Transdominant Inhibition of CCR5-Mediated HIV-1 Infection by CCR5Δ32," *J Biol Chem* 272:30603-30606 (1977).
Berger, et al., "Chemokine Receptors as HIV-1 Coreceptors: Roles In Viral Entry, Tropism, and Disease," *Annu Rev Immunology* 17:657-700 (1999).
Belfort, et al., "Homing Endonucleases: Keeping the House in Order," *Nucleic Acids Research* 25:3379-3388 (1997).
Bifinate, et al., "FOKI Dimerization is Required for DNA Cleavage," *PNAS USA* 95:10570-10575 (1998).
Chevalier, et al., "Design, Activity, and Structure of a Highly Specific Artificial Endonuclease," *Molecular Cell* 10:895-905 (2002).
Choo, et al., "Advances in Zinc Finger Engineering," *Curr. Opin. Struct. Biol.* 10:411-416 (2000).
Dean, et al., "Genetic Restriction of HIV-1 Infection and Progression to AIDS by a Deletion Allele of the CKR5 Structural Gene," *Science* 273:1856-1862 (1996).
Deng, et al., "Identification of a Major Co-Receptor for Primary Isolates of HIV-1," *Nature* 381:661-666 (1996).
Dragic, et al., "HIV-1 Entry Into CD4+ Cells is Mediated by the Chemokine Receptor CC-CKR-5," *Nature* 381(6584):667-673 (1996).
Dajon, et al., "Mobile Introns: Definition of Terms and Recommended Nomenclature," *Gene* 82:115-118 (1989).
Durai, et al., "Zinc Finger Nucleases: Custom-Designed Molecular Scissors for Genome Engineering of Plant and Mammalian Cells," *Nucl Acids Res* 33(18):5978-5990 (2005).
Epinat, et al., "A Novel Engineered Meganuclease Induces Homologous Recombination in Yeast and Mammalian Cells," *Nucleic Acids Research* 31:2952-2962 (2003).
Fatkenheuer, et al., "Efficacy of Short-Term Monotherapy With Maraviroc, a New CCR5 Antagonist, in Patients Infected With HIV-1," *Nat Med* 11:1170-1172 (2005).
Feng, et al., "Inhibition of CCR5-Dependent HIV-1 Infection by Hairpin Ribozyme Gene Therapy Against CC-Chemokine Receptor 5," *Virology* 276:271-278 (2000).
Fields, et al., "A Novel Genetic System to Detect Protein-Protein Interactions," *Nature* 340:245-246 (1989).
Gimble, et al., "Substrate Recognition and Induced DNA Distortion by the PI-SCEI Endonuclease, an Enzyme Generated by Protein Splicing," *J. Mol. Biol.* 263:163-180 (1996).
Gribskov, et al., "Sigma Factors from E. coli, B. subtilis, Phage SP01, and Phage T4 are Homologous Proteins," *Nucl Acids Res.* 14(6):6745-6763 (1986).
Huang, et al., "The Role of a Mutant CCR5 Allele in HIV-1 Transmission and Disease Progression," *Nat Med* 2:1240-1243 (1996).
Hung, et al., "Analysis of the Critical Domain in the V3 Loop of Human Immunodeficiency Virus Type 1 GP120 Involved in CCR5 Utilization," *J. Virology* 73:8216-8226 (1999).
Isalan et al., "A Rapid, Generally Applicable Method to Engineer Zinc Fingers Illustrated by Targeting the HIV-1 Promoter," *Nat Biotechnol* 19:656-660 (2001).
Jamieson, et al., "Drug Discovery With Engineered Zinc-Finger Proteins," *Nat Rev Drug Discov* 2:361-368 (2003).
Jasin, et al., "Genetic Manipulation of Genomes With Rare-Cutting Endonucleases," *Trends Genet* 12:224-228 (1996).
Kandavelou, et al., "Magic Scissors for Genome Surgery," *Nature Biotech* 23(6):686-687 (2005).
Kim, et al., "Insertion and Deletion Mutants of FOK1 Restriction Endonuclease," *J. Biol. Chem.* 269:31978-31981 (1994).
Kim, et al., "Chimeric Restriction Endonuclease," *PNAS USA* 91:883-887 (1994).
Kuhmann, et al., "Genetic and Phenotypic Analyses of Human Immunodeficiency Virus Type 1 Escape From a Small-Mollecule CCR5 Inhibitor," *J. Virol* 78:27900-2807 (2004).
Levine, et al., "Effects of CD28 Costimulation on Long-Term Proliferation of CD4+ T Cells in the Absence of Exogenous Feeder Cells," *J. Immunology* 159:5921-5930 (1997).
Levine, et al., "Gene Transfer in Humans Using a Conditionally Replication Lentiviral Vector," *PNAS USA* 103: 17372-17377 (2006).
Li, et al., "Functional Domains in FOK I Restriction Endonuclease," *PNAS USA* 89:4275-4279 (1992).
Li, et al., "Alteration of the Cleavage Distance of FOK I Restriction Endonuclease by Insertion Mutagenesis," *PNAS USA* 90:2764-2768 (1993).
Liu, et al., "Homozygous Defect in HIV-1 Coreceptor Accounts for Resistance of Some Multiply-Exposed Individuals to HIV-1 Infection," *Cell* 86:367-377 (1996).
Liu, et al., "Validated Zinc Finger Protein Designs for all 16 GNN DNA Triplet Targets," *J Biol Chem* 277(6):3850-3856 (2000).
Lombardo, et al., "Gene Editing in Human Stem Cells Using Zinc Finger Nucleases and Integrase-Defective Lentiviral Vector Delivery," *Nature Biotech* 25(11):12989-1306 (2007).
Mani, et al., "Design, Engineering, and Characterization of Zinc Finger Nucleases," *Biochem Biophys Res Comm* 352(2):447-457 (2005).
Momer, et al., "Primary Human Immunodeficiency Virus Type 2 (HIV-2) Isolates, Like HIV-1 Isolates, Frequently Use CCR5 but Show Promiscuity in Coreceptor Usage," *J. Virology* 73:2343-2349 (1999).
Ni, et al., "Evaluation of Biodistribution and Safety of Adenovirus Vectors Containing Group B Fibers After Intravenous Injection Into Baboons," *Hum Gene Ther* 16:664-677 (2005).
Nilsson, et al., "Functionally Distinct Subpopulations of Cord Blood CD34+ Cells are Transduced by Adenoviral Vectors With Serotpye 5 or 35 Tropism," *Mol Ther* 9:377-388 (2004).
Nilsson, et al., "Development of an Adenoviral Vector System With Adenovirus Serotype 35 Tropism; Efficient Transient Gene Transfer Into Primary Malignant Hematopoietic Cells," *J Gene Med* 6:631-641 (2004).
Oleykowski et al., "Mutation Detection Using a Novel Plant Endonuclease," *Nucleid Acids Research* 26:4597-4602 (1998).
Pabo, et al., "Design and Selection of Novel CYS2-HIS2 Zinc Finger Proteins," *Ann. Rev. Biochem.* 70:313-340 (2001).
Paques, et al., "Meganucleases and DNA Double-Strand Break-Induced Recombination: Perspectives for Gene Therapy," *Current Gene Therapy* 7:49-66 (2007).
Perez, et al., "Establishment of HIV-1 Resistance in CD4+ T Cells by Genome Editing Using Zinc-Finger Nucleases," *Nature Biotechnology* 26:808-816 (2008).
Perler, et al., "Protein Splicing Elements: Inteins and Exteins a Definition of Terms and Recommended Nomenclature," *Nucleic Acids Research* 22:1125-1127 (1994).
Peters, et al., "A Mechanism for the Impaired IFN-(Gamma) Production in C-C Chemokine Receptor 2 (CCR2) Knockout Mice: Role of CCR2 in Linking the Innate and Adaptive Immune Response," *J. Immunology* 165:7072-7077 (2000).
Porteus, et al., "Gene Targeting Using Zinc Finger Nucleases," *Nature Biotech* 23(8):967-973 (2005).
Qui, et al., "Mutation Detection Using Surveyor Nuclease" *Biotechniques* 36:702-707 (2004).
Reddy, et al., "Development of Adenovirus Serotype 35 as a Gene Transfer Vector," *Virology* 311:384-393 (2003).
Roberts, et al., "Rebase: Restriction Enzymes and Methyltransferases," *Nucleic Acids Research* 31:418-420 (2003).
Roseneeker et al., "Adenovirus Infection in Cystic Fibrosis Patients: Implications for the Use of Adenoviral Vectors for Gene Transfer," *Infection* 24:5-8 (1996).
Samson, et al., "Resistance to HIV-1 Infection in Caucasian Individuals Bearing Mutant Alleles of the CCR-5 Chemokine Receptor Gene," *Nature* 382:722-725 (1996).
Schroers, et al., "Gene Transfer Into Human T Lymphocytes and Natural Killer Cells by AD5/F35 Chimeric Adenoviral Vectors," *Exp Hematol* 32:536-546 (2004).

(56) References Cited

OTHER PUBLICATIONS

Schultz, et al., "P53 Binding Protein 1 (53BP1) is an Early Participant in the Cellular Response to DNA Double-Strand Breaks," *J Cell Biol* 151:1381-1390 (2000).

Segal, et al., "Custom DNA-Binding Proteins come of Age: Polydactyl Zinc-Finger Proteins," *Curr. Opin. Biotechnol.* 12:632-637 (2001).

Shayakhmetov, et al., "Efficient Gene Transfer Into Human CD34+ Cells by a Retargeted Adenovirus Vector," *J Virol* 74:2567-2583 (2004).

Smith, et al., "CCR2 Chemokine Receptor and AIDS Progression," *Nat. Med* 3:1052-1053 (1977).

Smith and Waterman, "Comparison of Biosequences," *Advances in Applied Mathematics* 2:482-489 (1981).

Sova, et al., "A Tumor-Targeted and Conditionally Replicating Oncolytic Adenovirus Vector Edxpressing Trail for Treatment of Liver Metastases," *Mol Ther* 9:496-509 (204).

Sterman, et al., "Adenovirus-Mediated Herpes Simplex Virus Thymiding Kinase/Ganciclovir Gene Therapy in Patients With Localized Malignancy: Results of a Phase 1 Clinical Trial in Malignant Mesothelioma," *Hum. Gene Ther.* 7:1083-1089 (1998).

Swan, et al., "Can Gene Delivery Close the Door to HIV-1 Entry After Escape?" *J Med Primitology* 35:236-247 (2006).

Topf, et al., "Regional 'Pro-Drug' Gene Therapy: Intravenous Administration of an Adenoviral Vector Expressing the *E. coli* Cytosine Deaminase Gene and Systemic Administration of 5-Fluorocytosine Suppresses Growth of Hepatic Metastasis of Colon Carcinoma," *Gene Ther* 5:507-513 (1998).

Trkola, et al., "HIV-1 Escape From a Small Molecule, CCR5-Specific Entry Inhibitor Does Not Involve CXCR4 Use," *PNAS USA* 99:395-400 (2002).

Urnov, et al., "Highly Efficient Endogenous Human Gene Correction Using Designed Zinc-Finger Nucleases," *Nature* 435:646-651 (2005).

Welsh, et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," *Hum. Gene Ther.* 2:205-218 (1995).

Yang, et al., "Phenotypic Knockout of HIV Type 1 Chemokine Coreceptor CCR-5 by Intrakines as Potential Therapeutic Approach for HIV-1 Infection," *PNAS USA* 94:11567-11572 (1997).

Yeung, et al., "Enzymatic Mutation Detection Technologies," *BioTechniques* 38:749-758 (2005).

\* cited by examiner

Ad5/35 vector: transgene expression cassette (GFP and ZFN) or donor sequence inserted in E1 region FIG. 2: Wild type FokI cleavage half domain QLVKSELEEKKSELRHKLKYVPHEYIELIEIARNSTQDRILEMKVMEFFMKVYGYRGKHLGGSRKPDGAIYTVGSPIDYGVIVDTKAYSGGYNL
PIGQADEMQRYVEENQTRNKHINPNEWWKVYPSSVTEFKFLFVSGHFKGNYKAQLTRLNHITNCNGAVLSVEELLIGGEMIKAGTLTLEEVRRK
FNNGEINF (SEQ ID NO:33)

FIG. 3: Q486E:I499L dimerization mutant

QLVKSELEEKKSELRHKLKYVPHEYIELIEIARNSTQDRILEMKVMEFFMKVYGYRGKHLGGSRKPDGAIYTVGSPIDYGVIVDTKAYSGGYNL
PIGQADEMERYVEENQTRNKHLNPNEWWKVYPSSVTEFKFLFVSGHFKGNYKAQLTRLNHITNCNGAVLSVEELLIGGEMIKAGTLTLEEVRRK
FNNGEINF (SEQ ID NO:34)

FIG. 4: E490K:I538K dimerization mutant

QLVKSELEEKKSELRHKLKYVPHEYIELIEIARNSTQDRILEMKVMEFFMKVYGYRGKHLGGSRKPDGAIYTVGSPIDYGVIVDTKAYSGGYNL
PIGQADEMQRYVKENQTRNKHINPNEWWKVYPSSVTEFKFLFVSGHFKGNYKAQLTRLNHKTNCNGAVLSVEELLIGGEMIKAGTLTLEEVRRK
FNNGEINF (SEQ ID NO:35)

FIG. 5 (SEQ ID NO: 36):
gttgtcaaagcttcattcactccatggtgctatagagcacaagatttatttggtgagatggtgctttcatgaattccccaacagagccaagc
tctccatcctagtgacaggaagctagcagcagcaacctccttcactacaaacttcattgcttgccaaaagagagttaattcaatgtagac
atctatgtaggcaattaaaaacctattgatgtataaaacagtttgcattcatgagggcaactaaatacattctaggacttatataaagatcac
tttttatttatgcacaggtggaacaagatgattatcaagtgtcaagtcctactctatgacatcattattatacatcgagccctgccaaaaa
atcaatgtgaagcaaatcgcagccccgcctctgcctccgctcactggtgttcatctttgttttgtgggcaacatgctggtcatcctca
tcctgataaactgcaaaggctgaagagcatgactacttggaaatacaatgtgtcaactcttgacaggctctattttatagcttctctctgaatc
ctggctcactatgctgccgcccagtcgataggtaccctggctgcgtcttgcccatgtcgtccatgtgcttgttgccagacagtcaccttggtgga
ttccttcatcatcctcctgacaatcgatagtcagtatctgtttgcgtcttctcccaggaatcatctttaaagatcatcttgggcgtgttcctgcgcttgtcatg
caagtgtgatcacttggtggtgtcactcagttcctcataatctgtcaatcctctaaaaaactctgctactcgtcttgaacactcttccttgcctgaatgtcagtagctctaa
ctcatcattttccatacagtcactaaaatctctaaaaactctgcttcctcgtctcctctgggctccctacaacattgtcctcctccaggaattcttttgcctgaataattgcctagctctaa
ttgtttattttctctctgggcttactctctctaaaactctgcttcctcgtctcctctgggctccctacaacattgtcctcctccaggaattcttttgcctgaataattgcctagctctaa
caggttggaccaagctatgcaggtgacaggctatgcaggtgacagactcttggatgacgcactgctgctcaaacccatcatcatctatgccttgtcgggagaagttc
agaaactacccttcagttctcttttctccaaaagcagcaggacagcagcagcagcaacgcttctgcaaatgctgttctcttctgttctctatttctccagcaagaggctcccgagcgagcaa
gctcagtttacacccgatcccactgggctggcctggctggtgggagagttcttttaaaaggaagttactgttatagagggtctaagatttgca
catggcttagttttcatacacacagtcgtttaagtagatcttttaaagcccatcaatcaaaatatgttgataaagaatagcaa
tccattttattttctcccctcacatgcatcaagttattgacaaactctccctcactccgaaagttccttatgtattttaaaagaaagcctcagag
ccttttttatctccccttgagttcttgagttagtgatctgaacagaaataccaaaattatttcagaaatgtacaactttttaccctagtacaaggcaacatatagg
aattgctgattcttgtttaaaacaggtctttgtcttgctatggggagaaagacatgaatgattagtaaagaaatgacactttcatgtgtgatttt
ttgtaaatgtgtttaaaacaggtctttgtcttgctatgggagaaagacatgaatgattagtaaagaaatgacactttcatgtgtgatttt
c FIG. 6 (SEQ ID NO: 37): 47bp CCR5 Patch sequence ctagatcagtgagtatgccctgatgctgtctgactgatgcctcgt

FIG. 7 (SEQ ID NO: 38):

```
gttgtcaaagcttcattcactccatggtgctatagagcacaagatttattggtgagatggtgcttcatgaattccccaacagagccaagc
tctccatctagtggacaggaagctagcagcagcaaacctccttcactacaaaacttcattgcttggccaaaagagagttaattcaatgtagac
atctatgtaggcaattaaaaacctattgatgtataaaacagtttgcattcatggaggcaactaaatacattctagaactttataaaagatcac
tttttatttatgcacaggtggaacaagatggattatcaagtgtcaagtccaatctatgacatcaattattatcatcgagccctgccaaaaa
atcaatgtgaagcaaatcgcagcccgcctcctgaacgctctactcacgtgttcatcttggttttttgtgggcaacatgctgactctacctca
tctagatcagtgagtatgcgcctgatgcgtctgactggcgtctttttccttcttactgtccccttctggctgtgcaaaagctgacatctacctg
ctcaacctggccatcctctgacctgctatttatagcttcttcctctgaatcttcttcatcctcctgacaatcgatagtacctgctgtcgtcca
gtcaactcttgacaggggctctatttaaaagccaggacgttcaccttgtgggtggtgacaagtgtgatcactttggtgctgtttttgctctctcccgga
tgctgttgcttttaccagatctcaaaaagaagcctctgccgctcattacaaacctgcttgtctggaatctgacaccagtcagtcattctgaagaattccaga
atcatcttaccagatctcaaaaagaagctcattacaccgtcctgccgctgtcctgtcatctgctactcggaatcctaaaaactctgcttcggtgtcgaaa
cattaaagatagtcatcttgggctgtcctgagcggctgagccttgagggctgaataattgcctaatgcagctctaacaggttgaccaagctatgcaggtgacagtgacagactcttggatgacgc
tgagagaggcacaggctggtttgcctgaataattgcctttgtcggggagaagttcagaaaactacctcttagtcttctcttccaaaagcacactctgtgggc
aacaccttccagaatctcttggcctgaataattgcctttgtcggggagaagttcagaaaactacctcttagtcttctcttccaaaagcacattgccaaacgctt
actgctgcatcaacccatcatctatgcctttgtcggggagaagctcccgagcgagcaagctcagttacaccgatcccagttgcttagtttcatacacagcccagttgcacaccatatctgtgggc
ctgcaaatgctgttctatttccagagagctccagcaagtcagcaagctcagttgccacatggctgcacatggctaagtcttaatcttgtttaaagtagattagatcttttaagccc
ttgtgacacggactcaagtggctggtgaccagtgaccagtgaggtgaccagtgtgccacatggccatccattttaataaagaagtcttttaattaaaggaagttactgttatagagggtctaaaaatgttgatgaaaaaataatgaaccaattattggcatcctgtttaagtagattagatcttttaagccc
atcaattatagaaagccaaatcaaatatgttgatgaaaaaataatgaacctcagaagaattgctgattcttgagttgatctgaacagaataccaaaatt
atttcagaaatgtacaactttttaccctagtacaaggcaacatataggttgtaaatgtgtttaaaacaggtcttgttctgtatgggagaaaa
gacatgaatatgattagtacaaactttcatgtgtgattttc
```

```
                                                                                                                              SEQ
                                                                                                                              ID
                                                                                                                              NO
ysy24   deletion  PBMC    TTTTGTGGGCAACATGCTGGTCATC............................AGCAAAAGGCTGAAGAGCATGACTGACATCTACCTGCTC  54
ysy12   deletion  PBMC    TTTTGTGGGCAACATGCTGGTCATCCCTC........................AAGGCTGAAGAGCATGACTGACATCTACCTGCTC  55
lysy4   deletion  PBMC    TTTTGTGGGCAACATGCTGGTCATCCTCAT.......AAACTGCAAAAGGCTGAAGAGCATGACTGACATCTACCTGCTC  56
ysy19   deletion  PBMC    TTTTGTGGGCAACATGCTGGTCATCCTCATCCT....AAACTGCAAAAGGCTGAAGAGCATGACTGACATCTACCTGCTC  57
ysy58   deletion  T-Cell  TTTTGTGGGCAACATGCTGGTCATCCTCATCCT....AAACTGCAAAAGGCTGAAGAGCATGACTGACATCTACCTGCTC  57
ysy34   deletion  T-Cell  TTTTGTGGGCAACATGCTGGTCATCCTCATCCTG.......CAAAAGGCTGAAGAGCATGACTGACATCTACCTGCTC  58
ysy45   deletion  T-Cell  TTTTGTGGGCAACATGCTGGTCATCCTCATCCTG.......CAAAAGGCTGAAGAGCATGACTGACATCTACCTGCTC  58
ysy27   deletion  PBMC    TTTTGTGGGCAACATGCTGGTCATCCTCATCCTG..AAACTGCAAAAGGCTGAAGAGCATGACTGACATCTACCTGCTC  59
ysy37   deletion  T-Cell  TTTTGTGGGCAACATGCTGGTCATCCTCATCCTG..AAACTGCAAAAGGCTGAAGAGCATGACTGACATCTACCTGCTC  59
ysy59   deletion  T-Cell  TTTTGTGGGCAACATGCTGGTCATCCTCATCCTG.AAAACTGCAAAAGGCTGAAGAGCATGACTGACATCTACCTGCTC  60
lysy20  deletion  T-Cell  TTTTGTGGGCAACATGCTGGTCATCCTCATCCTGA.....CAAGAGCATGACTGACATGACTGACATCTACCTGCTC  61
lysy15  deletion  PBMC    TTTTGTGGGCAACATGCTGGTCATCCTCATCCTGAT......AGAGCATGACTGACATGACTGACATCTACCTGCTC  62
lysy10  deletion  PBMC    TTTTGTGGGCAACATGCTGGTCATCCTCATCCTGAT........AAAAGGCTGAAGAGCATGACTGACATCTACCTGCTC  63
ysy30   deletion  PBMC    TTTTGTGGGCAACATGCTGGTCATCCTCATCCTGAT........AAAAGGCTGAAGAGCATGACTGACATCTACCTGCTC  63
ysy13   deletion  PBMC    TTTTGTGGGCAACATGCTGGTCATCCTCATCCTGATA.........TGAAGAGCATGACTGACATCTACCTGCTC  64
ysy51   deletion  T-Cell  TTTTGTGGGCAACATGCTGGTCATCCTCATCCTGATAA..CTGCAAAAGGCTGAAGAGCATGACTGACATCTACCTGCTC  65
ysy63   deletion  T-Cell  TTTTGTGGGCAACATGCTGGTCATCCTCATCCTGATAA..CTGCAAAAGGCTGAAGAGCATGACTGACATCTACCTGCTC  65
ysy23   deletion  PBMC    TTTTGTGGGCAACATGCTGGTCATCCTCATCCTGATAAA.......GGCTGAAGAGCATGACTGACATCTACCTGCTC  66
```

FIG. 8

|  |  |  | Sequence | SEQ ID NO |
|---|---|---|---|---|
| ysy18 | insertion | PBMC | TTTTGTGGGCAACATGCTGGTCATCCTCATCCTGATGATAAACTGCAAAAGGCTGAAGAGCATGACTGACATCTACCTGCTC | 43 |
| lysy14 | insertion | PBMC | TTTTGTGGGCAACATGCTGGTCATCCTCATCCTCTAGATAAACTGCAAAAGGCTGAAGAGCATGACTGACATCTACCTGCTC | 44 |
| lysy34 | insertion | T-Cell | TTTTGTGGGCAACATGCTGGTCATCCTCATCCTCTAGATAAACTGCAAAAGGCTGAAGAGCATGACTGACATCTACCTGCTC | 44 |
| ysy14 | insertion | PBMC | TTTTGTGGGCAACATGCTGGTCATCCTCATCCTCTAGATAAACTGCAAAAGGCTGAAGAGCATGACTGACATCTACCTGCTC | 44 |
| ysy21 | insertion | PBMC | TTTTGTGGGCAACATGCTGGTCATCCTCATCCTCTAGATAAACTGCAAAAGGCTGAAGAGCATGACTGACATCTACCTGCTC | 44 |
| ysy25 | insertion | PBMC | TTTTGTGGGCAACATGCTGGTCATCCTCATCCTCTAGATAAACTGCAAAAGGCTGAAGAGCATGACTGACATCTACCTGCTC | 44 |
| ysy26 | insertion | PBMC | TTTTGTGGGCAACATGCTGGTCATCCTCATCCTCTAGATAAACTGCAAAAGGCTGAAGAGCATGACTGACATCTACCTGCTC | 44 |
| ysy29 | insertion | PBMC | TTTTGTGGGCAACATGCTGGTCATCCTCATCCTCTAGATAAACTGCAAAAGGCTGAAGAGCATGACTGACATCTACCTGCTC | 44 |
| ysy57 | insertion | T-Cell | TTTTGTGGGCAACATGCTGGTCATCCTCATCCTCTAGATAAACTGCAAAAGGCTGAAGAGCATGACTGACATCTACCTGCTC | 44 |
| ysy7 | insertion | PBMC | TTTTGTGGGCAACATGCTGGTCATCCTCATCCTCTAGATAAACTGCAAAAGGCTGAAGAGCATGACTGACATCTACCTGCTC | 44 |
| ysy9 | insertion | PBMC | TTTTGTGGGCAACATGCTGGTCATCCTCATCCTCTAGATAAACTGCAAAAGGCTGAAGAGCATGACTGACATCTACCTGCTC | 44 |
| ysy28 | insertion | PBMC | TTTTGTGGGCAACATGCTGGTCATCCTCATCGTGATGTGATAAACTGCAAAAGGCTGAAGAGCATGACTGACATCTACCTGCTC | 46 |

|  |  |  | Sequence | SEQ ID NO |
|---|---|---|---|---|
| lysy7 | insertion | PBMC | TTTTGTGGGCAACATGCTGGTCATCCTCATCCTGA.CTGATAAACTGCAAAAGGCTGAAGAGCATGACTGACATCTACCTGCTC | 47 |
| lysy24 | insertion | T-Cell | TTTTGTGGGCAACATGCTGGTCATCCTCATCCTCATCCTGATAAAAACTGCAAAAGGCTGAAGAGCATGACTGACATCTACCTGCTC | 48 |
| ysy35 | insertion | T-Cell | TTTTGTGGGCAACATGCTGGTCATCCTCATCCTCATCCTGATAAAACTGCAAAAGGCTGAAGAGCATGACTGACATCTACCTGCTC | 49 |
| lysy33 | insertion | T-Cell | TTTTGTGGGCAACATGCTGGTCATCCTCATCCTCATCCTGATATAAACTGCAAAAGGCTGAAGAGCATGACTGACATCTACCTGCTC | 50 |

FIG. 9

| | | | |
|---|---|---|---|
| ysy38 | insertion | T-Cell | TTTTGTGGGTAACATGCTGGTCATCCTCATCTAGATCAGTGAGTATGCCCTGATGGCGTCTGGACTGGATGCCTGCCTAGAAACTG 51<br>CAAAAGGCTGAAGAGCATGACTGACATCTACCTGCTC |
| ysy56 | insertion | T-Cell | TTTTGTGGGCAACATGCTGGTCATCCTCATCCTCCTTCTAGATCAGTGAGTATGCCCTGATGGCGTCTGGACTGGATGCCTCGTCTAGATA 52<br>AACTGCAAAAGGCTGAAGAGCATGACTGACATCTACCTGCTC |
| ysy61 | insertion | T-Cell | TTTTGTGGGCAACATGCTGGTCATCCTCATCCTTCTAGATCAGTGAGTATGCCCTGATGGCGTCTGGACTGGATGCCTCGTCTAGATA 52<br>AACTGCAAAAGGCTGAAGAGCATGACTGACATCTACCTGCTC |
| lysy3 | insertion | PBMC | TTTTGTGGGCAACATGCTGGTCATCCTCATCCTGATGCCCTGCAGGTGCACCACAGAGCTCACCCAACCTGAGTCCCTCTGGTACT 53<br>GACCACTCCAGACTGAGTCCCTCTGGTACTGACCACTCCGGACTGAGTCCCTCTGGTACTGACCACTCCAGGGCTCTGATAAACTGCAA<br>AAGGCTGAAGAGCATGACTGACATCTACCTGCTC |

FIG. 10

FIG. 12 (SEQ ID NOS: 67 and 68)

| DELETIONS: | | SEQ ID |
|---|---|---|
| TTTTGTGGGCAACATGCTGGTCATCCTCATCCTGATAAACTGCAAAAGGCTGAAGAGCATGACTGACATCTACCTGCTC | w.t. | 80 |
| TTTTGTGGGCAACATGCTGGTCATCCTCATCCTGATAAACTGCAAAAGGCTGAAGAGCATGACTGACATCTACCTGCTC | -1 | 69 |
| TTTTGTGGGCAACATGCTGGTCATCCTCATCCTG--AAACTGCAAAAGGCTGAAGAGCATGACTGACATCTACCTGCTC | -2 | 59 |
| TTTTGTGGGCAACATGCTGGTCATCCTCATCCT--TAAACTGCAAAAGGCTGAAGAGCATGACTGACATCTACCTGCTC | -2 | 70 |
| TTTTGTGGGCAACATGCTGGTCATCCTCATCCTC--GATAAACTGCAAAAGGCTGAAGAGCATGACTGACATCTACCTGCTC | -2 | 73 |
| TTTTGTGGGCAACATGCTGGTCATCCTCATCCTCA--CTGATAAACTGCAAAAGGCTGAAGAGCATGACTGACATCTACCTGCTC | -2 | 74 |
| TTTTGTGGGCAACATGCTGGTCATCCTCATCCTCATC---TAAACTGCAAAAGGCTGAAGAGCATGACTGACATCTACCTGCTC | -3 | 75 |
| TTTTGTGGGCAACATGCTGGTCATCCTCATCCTCATC----ATAAACTGCAAAAGGCTGAAGAGCATGACTGACATCTACCTGCTC | -4 | 76 |
| TTTTGTGGGCAACATGCTGGTCATCCTCATCCTCATCC----AAACTGCAAAAGGCTGAAGAGCATGACTGACATCTACCTGCTC | -4 | 77 |
| TTTTGTGGGCAACATGCTGGTCATCCTCATCCTCATC-----AAACTGCAAAAGGCTGAAGAGCATGACTGACATCTACCTGCTC | -5 | 78 |
| TTTTGTGGGCAACATGCTGGTCATCCTCATCCTCA------ATAAACTGCAAAAGGCTGAAGAGCATGACTGACATCTACCTGCTC | -5 | 84 |
| TTTTGTGGGCAACATGCTGGTCATCCTCATCCTCATC-------TGATAAACTGCAAAAGGCTGAAGAGCATGACTGACATCTACCTGCTC | -7 | 85 |
| TTTTGTGGGCAACATGCTGGTCATCCTCATCC-------GATAAACTGCAAAAGGCTGAAGAGCATGACTGACATCTACCTGCTC | -7 | 86 |
| TTTTGTGGGCAACATGCTGGTCATCCTCATCCTCATCC----------TGATAAACTGCAAAAGGCTGAAGAGCATGACTGACATCTACCTGCTC | -10 | 87 |
| TTTTGTGGGCAACATGCTGGTCATCCTCATC--------GATAAACTGCAAAAGGCTGAAGAGCATGACTGACATCTACCTGCTC | -8 | 88 |
| TTTTGTGGGCAACATGCTGGTCATCCTCATCCTC---------AACTGCAAAAGGCTGAAGAGCATGACTGACATCTACCTGCTC | -9 | 89 |
| TTTTGTGGGCAACATGCTGGTCATCCTCATCCTCATCCTGAT-----GCAAAAGGCTGAAGAGCATGACTGACATCTACCTGCTC | -5 | 90 |
| TTTTGTGGGCAACATGCTGGTCATCCTCATCCTCATCC-----------AAAAGGCTGAAGAGCATGACTGACATCTACCTGCTC | -11 | 91 |
| TTTTGTGGGCAACATGCTGGTCATCCTCATCCTCATCCTGAT-------AAAGGCTGAAGAGCATGACTGACATCTACCTGCTC | -7 | 63 |
| TTTTGTGGGCAACATGCTGGTCATCCTCATCCTCATCCTGAT--------AAGGCTGAAGAGCATGACTGACATCTACCTGCTC | -8 | 66 |
| TTTTGTGGGCAACATGCTGGTCATCCTCATCCTCATCCTGA------------AGAGAGCATGACTGACATCTACCTGCTC | -18 | 92 |
| TTTTGTGGGCAACATGCTGGTCATCCTCATC------------------CTGAAGAGCATGACTGACATCTACCTGCTC | -20 | 93 |
| TTTTGTAGGCAACATGCTGGTCATCCTG---------------------ACTGCAAAAGGCTGAAGAGCATGACTGACATCTACCTGCTC | -19 | 94 |
| TTTTGTGGGCAACATGC-----------------GTAAACTGCAAAAGGCTGAAGAGCATGACTGACATCTACCTGCTC | -17 | 95 |
| TTTTGTGGGCAACATGC----------------TGCAAACTGCAAAAGGCTGAAGAGCATGACTGACATCTACCTGCTC | -16 | 96 |
| TTTTGTGGGCAACATGCTGGTC-----------TAAACTGCAAAAGGCTGAAGAGCATGACTGACATCTACCTGCTC | -13 | 97 |
| TTTTGTGGGCAACATGCTGGTCA---------------------AAAAGGCTGAAGAGCATGACTGACATCTACCTGCTC | -21 | 98 |
| TTTTGTGGGCAACATGC---------------------AAAAGGCTGAAGAGCATGACTGACATCTACCTGCTC | -26 | 99 |
| TTTTGTGGGCAACATG-----------------------------AAAGGCTGAAGAGCATGACTGACATCTACCTGCTC | -36 | 100 |
| TTTTGTGGGCAACAT-------------------------------------ATGACTGACATCTACCTGCTC | -43 | 101 |

| INSERTIONS: | | |
|---|---|---|
| TTTTGTGGGCAACATGCTGGTCATCCTCATCCTGATAAACTGCAAAAGGCTGAAGAGCATGACTGACATCTACCTGCTC | w.t. | 80 |
| TTTTGTGGGCAACATGCTGGTCATCCTCATCCTCATCCTGATAtAAACTGCAAAAGGCTGAAGAGCATGACTGACATCTACCTGC | +2 | 102 |
| TTTTGTGGGCAACATGCTGGTCATCCTCATCCTCATCCTGATAaAAACTGCAAAAGGCTGAAGAGCATGACTGACATCTACCTGC | +2 | 103 |
| TTTTGTGGGCAACATGCTGGTCATCCTCATCCTCATCCTGATgatAAACTGCAAAAGGCTGAAGAGCTGAAGAGCATGACATCTACCTG | +3 | 104 |
| TTTTGTGGGCAACATGCTGGTCATCCTCATCCTCATCCTGActgaTAAACTGCAAAAGGCTGAAGAGCTGAAGAGCATGACATGACATCTACCT | +4 | 105 |
| TTTTGTGGGCAACATGCTGGTCATCCTCATCCTCATCCTGATtgatAAACTGCAAAAGGCTGAAGAGCATGAGCATGACTGACATCTACCT | +4 | 106 |
| TTTTGTGGGCAACATGCTGGTCATCCTCATCCTCATCCTGATctgataAACTGCAAAAGGCTGAAGAGCATGAAGAGCATGACATCTACC | +5 | 107 |
| TTTTGTGGGCAACATGCTGGTCATCCTCATCCTCATCCTCATCttaatttaATAAACTGCAAAAGGCTGAAGAGCATGACATGACTCTACC | +8 | 108 |

FIG. 16

FIG. 17
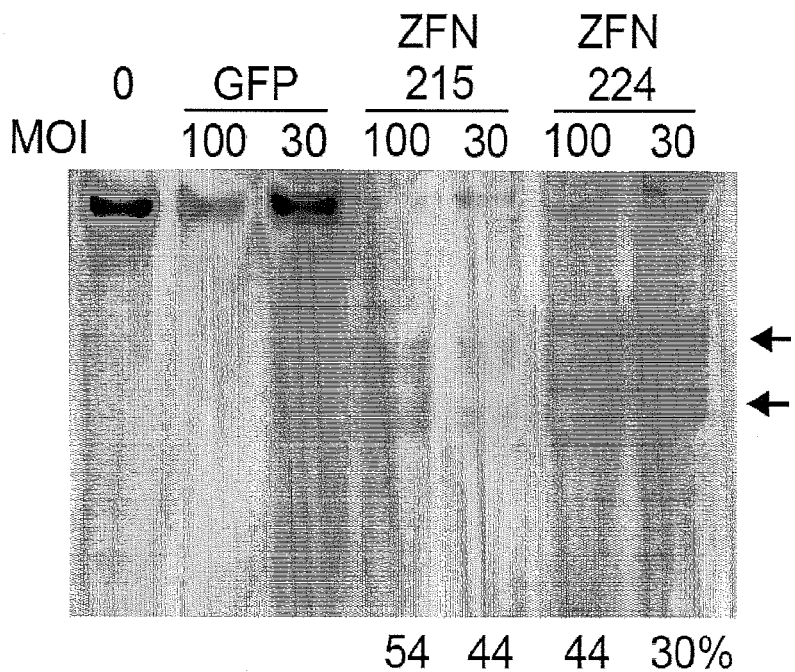
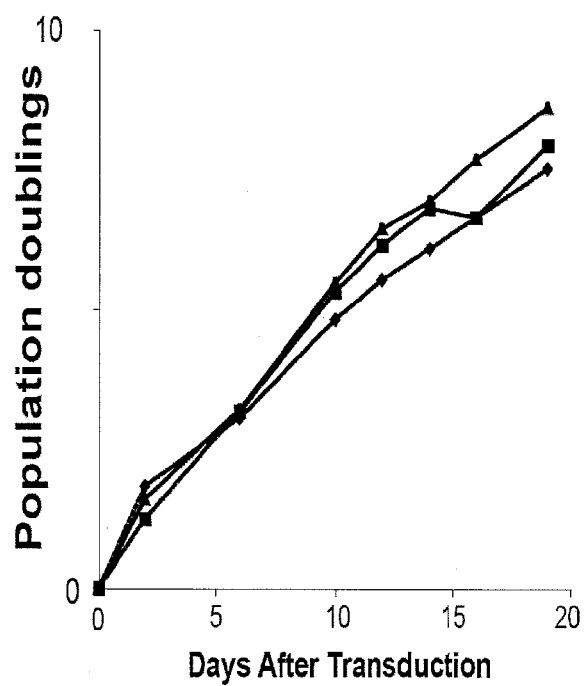
FIG. 18

SEQUENCE LISTING

```
<160> NUMBER OF SEQ ID NOS: 108

<210> SEQ ID NO 1
<211> LENGTH: 12
<212> TYPE: DNA
<213> ORGANISM: Artificial Sequence
<220> FEATURE:
<223> OTHER INFORMATION: zinc finger target sequence in human CCR-5 gene

<400> SEQUENCE: 1
gatgaggatg ac                                                         12

<210> SEQ ID NO 2
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 2

Asp Arg Ser Asn Leu Ser Arg
1               5

<210> SEQ ID NO 3
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 3

Thr Ser Ala Asn Leu Ser Arg
1               5

<210> SEQ ID NO 4
<211> LENGTH: 7
<212> TYPE: PRT
<213> ORGANISM: Artificial Sequence
<220> FEATURE:
```

```
<223> OTHER INFORMATION: zinc finger binding domain

<400> SEQUENCE: 4

Arg Ser Asp Asn Leu Ala Arg
1               5

<210> SEQ ID NO 5
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 5

Ile Ser Ser Asn Leu Asn Ser
1               5

<210> SEQ ID NO 6
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 6

Val Ser Ser Asn Leu Thr Ser
1               5

<210> SEQ ID NO 7
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 7

Asn Arg Asp Asn Leu Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 8

Thr Ser Gly Asn Leu Thr Arg
1               5

<210> SEQ ID NO 9
<211> LENGTH: 12
<212> TYPE: DNA
<213> ORGANISM: Artificial Sequence
<220> FEATURE:
<223> OTHER INFORMATION: zinc finger target sequence in human CCR-5 gene

<400> SEQUENCE: 9
aaactgcaaa ag                                                         12

<210> SEQ ID NO 10
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 10
```

```
Arg Ser Asp Asn Leu Ser Val
1               5

<210> SEQ ID NO 11
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 11

Gln Asn Ala Asn Arg Ile Thr
1               5

<210> SEQ ID NO 12
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 12

Arg Ser Asp Val Leu Ser Glu
1               5

<210> SEQ ID NO 13
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 13

Gln Arg Asn His Arg Thr Thr
1               5

<210> SEQ ID NO 14
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 14

Arg Ser Asp Asn Leu Ser Asn
1               5

<210> SEQ ID NO 15
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 15

Gln Arg Val Asn Leu Ile Val
1               5

<210> SEQ ID NO 16
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 16

Arg Ser Asp Asn Leu Gly Val
```

<210> SEQ ID NO 17
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 17

Gln Lys Ile Asn Leu Gln Val
1               5

<210> SEQ ID NO 18
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 18

Arg Ser Asp His Leu Ser Glu
1               5

<210> SEQ ID NO 19
<211> LENGTH: 12
<212> TYPE: DNA
<213> ORGANISM: Artificial Sequence
<220> FEATURE:
<223> OTHER INFORMATION: zinc finger target sequence in human CCR-5 gene

<400> SEQUENCE: 19
gacaagcagc gg                                                         12

<210> SEQ ID NO 20
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 20

Arg Ser Ala His Leu Ser Glu
1               5

<210> SEQ ID NO 21
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 21

Arg Ser Ala Asn Leu Ser Glu
1               5

<210> SEQ ID NO 22
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 22

Arg Ser Ala Asn Leu Ser Val
1               5

-continued

```
<210> SEQ ID NO 23
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 23

Asp Arg Ala Asn Leu Ser Arg
1               5

<210> SEQ ID NO 24
<211> LENGTH: 13
<212> TYPE: DNA
<213> ORGANISM: Artificial Sequence
<220> FEATURE:
<223> OTHER INFORMATION: zinc finger target sequence in human CCR-5 gene

<400> SEQUENCE: 24
catctgctac tcg                                                          13

<210> SEQ ID NO 25
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 25

Arg Ser Asp Ser Leu Ser Lys
1               5

<210> SEQ ID NO 26
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 26

Asp Asn Ser Asn Arg Ile Lys
1               5

<210> SEQ ID NO 27
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 27

Arg Ser Ala Val Leu Ser Glu
1               5

<210> SEQ ID NO 28
<211> LENGTH: 7
<212> TYPE: PRT
<213> ORGANISM: Artificial Sequence
<220> FEATURE:
<223> OTHER INFORMATION: zinc finger binding domain

<400> SEQUENCE: 28

Thr Asn Ser Asn Arg Ile Thr
1               5

<210> SEQ ID NO 29
<211> LENGTH: 26
<212> TYPE: DNA
```

```
<213> ORGANISM: Artificial Sequence
<220> FEATURE:
<223> OTHER INFORMATION: Synthetic primer

<400> SEQUENCE: 29
aagatggatt atcaagtgtc aagtcc                                          26

<210> SEQ ID NO 30
<211> LENGTH: 17
<212> TYPE: DNA
<213> ORGANISM: Artificial Sequence
<220> FEATURE:
<223> OTHER INFORMATION: Synthetic primer

<400> SEQUENCE: 30
caaagtccca ctgggcg                                                    17

<210> SEQ ID NO 31
<211> LENGTH: 23
<212> TYPE: DNA
<213> ORGANISM: Artificial Sequence
<220> FEATURE:
<223> OTHER INFORMATION: Synthetic primer

<400> SEQUENCE: 31
ctgcctcata aggttgccct aag                                             23

<210> SEQ ID NO 32
<211> LENGTH: 29
<212> TYPE: DNA
<213> ORGANISM: Artificial Sequence
<220> FEATURE:
<223> OTHER INFORMATION: Synthetic primer

<400> SEQUENCE: 32
ccagcaatag atgatccaac tcaaattcc                                       29

<210> SEQ ID NO 33
<211> LENGTH: 196
<212> TYPE: PRT
<213> ORGANISM: Planomicrobium okeanokoites

<400> SEQUENCE: 33

Gln Leu Val Lys Ser Glu Leu Glu Glu Lys Lys Ser Glu Leu Arg His
 1               5                  10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
```

```
            145                 150                 155                 160
Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 34
<211> LENGTH: 196
<212> TYPE: PRT
<213> ORGANISM: Artificial Sequence
<220> FEATURE:
<223> OTHER INFORMATION: engineered FokI cleavage half-domain with Q486E
      and I499L mutations

<400> SEQUENCE: 34

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asn Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 35
<211> LENGTH: 196
<212> TYPE: PRT
<213> ORGANISM: Artificial Sequence
<220> FEATURE:
<223> OTHER INFORMATION: engineered FokI cleavage half-domain with E490K
      and I538K mutations

<400> SEQUENCE: 35

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45
```

```
Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 36
<211> LENGTH: 1881
<212> TYPE: DNA
<213> ORGANISM: Homo sapiens

<400> SEQUENCE: 36
gttgtcaaag cttcattcac tccatggtgc tatagagcac aagatttat  ttggtgagat     60 ggtgctttca tgaattcccc caacagagcc aagctctcca tctagtggac agggaagcta    120
gcagcaaacc ttcccttcac tacaaaactt cattgcttgg ccaaaaagag agttaattca    180
atgtagacat ctatgtaggc aattaaaaac ctattgatgt ataaaacagt ttgcattcat    240
ggagggcaac taaatacatt ctaggacttt ataaaagatc acttttttatt tatgcacagg    300 gtggaacaag atggattatc aagtgtcaag tccaatctat gacatcaatt attatacatc    360
ggagccctgc caaaaaatca atgtgaagca aatcgcagcc cgcctcctgc ctccgctcta    420
ctcactggtg ttcatctttg gttttgtggg caacatgctg gtcatcctca tcctgataaa    480
ctgcaaaagg ctgaagagca tgactgacat ctacctgctc aacctggcca tctctgacct    540 gttttttcctt cttactgtcc ccttctgggc tcactatgct gccgcccagt gggactttgg    600
aaatacaatg tgtcaactct tgacagggct ctatttata ggcttcttct ctggaatctt    660
cttcatcatc ctcctgacaa tcgataggta cctggctgtc gtccatgctg tgtttgcttt    720
aaaagccagg acggtcacct tggggtggt gacaagtgtg atcacttggg tggtggctgt    780
gtttgcgtct ctcccaggaa tcatctttac cagatctcaa aaagaaggtc ttcattacac    840
ctgcagctct catttttccat acagtcagta tcaattctgg aagaatttcc agacattaaa    900
gatagtcatc ttggggctgg tcctgccgct gcttgtcatg gtcatctgct actcgggaat    960
cctaaaaact ctgcttcggt gtcgaaatga aagaagagg cacagggctg tgaggcttat   1020
cttcaccatc atgattgttt attttctctt ctgggctccc tacaacattg tccttctcct   1080
gaacaccttc caggaattct ttggcctgaa taattgcagt agctctaaca ggttggacca   1140
agctatgcag gtgacagaga ctcttgggat gacgcactgc tgcatcaacc ccatcatcta   1200
tgcctttgtc ggggagaagt tcagaaacta cctcttagtc ttcttccaaa agcacattgc   1260
```

| | |
|---|---|
| caaacgcttc tgcaaatgct gttctatttt ccagcaagag gctcccgagc gagcaagctc | 1320 |
| agtttacacc cgatccactg gggagcagga aatatctgtg ggcttgtgac acggactcaa | 1380 |
| gtgggctggt gacccagtca gagttgtgca catggcttag ttttcataca cagcctgggc | 1440 |
| tgggggtggg gtgggagagg tctttttaa aaggaagtta ctgttataga gggtctaaga | 1500 |
| ttcatccatt tatttggcat ctgtttaaag tagattagat cttttaagcc catcaattat | 1560 |
| agaaagccaa atcaaaatat gttgatgaaa aatagcaacc ttttatctc cccttcacat | 1620 |
| gcatcaagtt attgacaaac tctcccttca ctccgaaagt tccttatgta tatttaaaag | 1680 |
| aaagcctcag agaattgctg attcttgagt ttagtgatct gaacagaaat accaaaatta | 1740 |
| tttcagaaat gtacaacttt ttacctagta caaggcaaca tataggttgt aaatgtgttt | 1800 |
| aaaacaggtc tttgtcttgc tatggggaga aaagacatga atatgattag taaagaaatg | 1860 |
| acacttttca tgtgtgattt c | 1881 |

<210> SEQ ID NO 37
<211> LENGTH: 47
<212> TYPE: DNA
<213> ORGANISM: Artificial Sequence
<220> FEATURE:
<223> OTHER INFORMATION: donor sequence for targeted insertion into the
    CCR-5 gene

<400> SEQUENCE: 37

| | |
|---|---|
| ctagatcagt gagtatgccc tgatggcgtc tggactggat gcctcgt | 47 |

<210> SEQ ID NO 38
<211> LENGTH: 1928
<212> TYPE: DNA
<213> ORGANISM: Artificial Sequence
<220> FEATURE:
<223> OTHER INFORMATION: human CCR-5 with patch sequence insertion

<400> SEQUENCE: 38

| | |
|---|---|
| gttgtcaaag cttcattcac tccatggtgc tatagagcac aagatttat ttggtgagat | 60 |
| ggtgctttca tgaattcccc caacagagcc aagctctcca tctagtggac agggaagcta | 120 |
| gcagcaaacc ttcccttcac tacaaaactt cattgcttgg ccaaaaagag agttaattca | 180 |
| atgtagacat ctatgtaggc aattaaaaac ctattgatgt ataaaacagt ttgcattcat | 240 |
| ggagggcaac taaatacatt ctaggacttt ataaaagatc acttttatt tatgcacagg | 300 |
| gtggaacaag atggattatc aagtgtcaag tccaatctat gacatcaatt attatacatc | 360 |
| ggagccctgc caaaaaatca atgtgaagca atcgcagcc cgcctcctgc ctccgctcta | 420 |
| ctcactggtg ttcatctttg gttttgtggg caacatgctg gtcatcctca tctagatcag | 480 |
| tgagtatgcc ctgatggcgt ctggactgga tgcctcgtct agataaactg caaaaggctg | 540 |
| aagagcatga ctgacatcta cctgctcaac ctggccatct ctgacctgtt tttccttctt | 600 |
| actgtccct tctgggctca ctatgctgcc gcccagtggg actttggaaa tacaatgtgt | 660 |
| caactcttga cagggctcta ttttataggc ttcttctctg gaatcttctt catcatcctc | 720 |
| ctgacaatcg ataggtacct ggctgtcgtc catgctgtgt ttgctttaaa agccaggacg | 780 |
| gtcacctttg ggtggtgac aagtgtgatc acttgggtgg tggctgtgtt tgcgtctctc | 840 |
| ccaggaatca tctttaccag atctcaaaaa gaaggtcttc attacacctg cagctctcat | 900 |
| tttccataca gtcagtatca attctggaag aatttccaga cattaaagat agtcatcttg | 960 |
| gggctggtcc tgccgctgct tgtcatggtc atctgctact cgggaatcct aaaaactctg | 1020 |

-continued

```
cttcggtgtc gaaatgagaa gaagaggcac agggctgtga ggcttatctt caccatcatg    1080
attgtttatt ttctcttctg ggctccctac aacattgtcc ttctcctgaa caccttccag    1140
gaattctttg gcctgaataa ttgcagtagc tctaacaggt tggaccaagc tatgcaggtg    1200
acagagactc ttgggatgac gcactgctgc atcaacccca tcatctatgc ctttgtcggg    1260
gagaagttca gaaactacct cttagtcttc ttccaaaagc acattgccaa acgcttctgc    1320
aaatgctgtt ctattttcca gcaagaggct cccgagcgag caagctcagt ttacacccga    1380
tccactgggg agcaggaaat atctgtgggc ttgtgacacg gactcaagtg gctggtgac    1440 ccagtcagag ttgtgcacat ggcttagttt catacacag cctgggctgg gggtggggtg    1500
ggagaggtct ttttttaaaag gaagttactg ttatagaggg tctaagattc atccatttat    1560
ttggcatctg tttaaagtag attagatctt ttaagcccat caattataga aagccaaatc    1620
aaaatatgtt gatgaaaaat agcaacctt ttatctcccc ttcacatgca tcaagttatt    1680
gacaaactct cccttcactc cgaaagttcc ttatgtatat ttaaaagaaa gcctcagaga    1740
attgctgatt cttgagttta gtgatctgaa cagaaatacc aaaattattt cagaaatgta    1800 caactttta cctagtacaa ggcaacatat aggttgtaaa tgtgtttaaa acaggtcttt    1860
gtcttgctat ggggagaaaa gacatgaata tgattagtaa agaaatgaca cttttcatgt    1920
gtgatttc                                                              1928

<210> SEQ ID NO 39
<211> LENGTH: 10
<212> TYPE: DNA
<213> ORGANISM: Artificial Sequence
<220> FEATURE:
<223> OTHER INFORMATION: nucleotides 470-479 in the CCR-5 donor fragment

<400> SEQUENCE: 39
atcctgataa                                                                10

<210> SEQ ID NO 40
<211> LENGTH: 10
<212> TYPE: DNA
<213> ORGANISM: Artificial Sequence
<220> FEATURE:
<223> OTHER INFORMATION: engineered XbaI recognition site

<400> SEQUENCE: 40
atctagataa                                                                10

<210> SEQ ID NO 41
<211> LENGTH: 29
<212> TYPE: DNA
<213> ORGANISM: Homo sapiens

<400> SEQUENCE: 41
gtcatcctca tcctgataaa ctgcaaaag                                           29

<210> SEQ ID NO 42
<211> LENGTH: 34
<212> TYPE: DNA
<213> ORGANISM: Artificial Sequence
<220> FEATURE:
<223> OTHER INFORMATION: human CCR-5 sequence with insertion of 5
      nucleotides

<400> SEQUENCE: 42
gtcatcctca tcctgatctg ataaactgca aaag                                     34
```

```
<210> SEQ ID NO 43
<211> LENGTH: 82
<212> TYPE: DNA
<213> ORGANISM: Artificial Sequence
<220> FEATURE:
<223> OTHER INFORMATION: human CCR-5 sequence with insertion of 4
      nucleotides

<400> SEQUENCE: 43
ttttgtgggc aacatgctgg tcatcctcat cctgatgata aactgcaaaa ggctgaagag      60
catgactgac atctacctgc tc                                               82

<210> SEQ ID NO 44
<211> LENGTH: 83
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 44
ttttgtgggc aacatgctgg tcatcctcat ccttctagat aaactgcaaa aggctgaaga      60
gcatgactga catctacctg ctc                                              83

<210> SEQ ID NO 45
<211> LENGTH: 33
<212> TYPE: DNA
<213> ORGANISM: Artificial Sequence
<220> FEATURE:
<223> OTHER INFORMATION: human CCR-5 sequence with insertion of 4
      nucleotides

<400> SEQUENCE: 45
gtcatcctca tccttctaga taaactgcaa aag                                   33

<210> SEQ ID NO 46
<211> LENGTH: 84
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 46
ttttgtgggc aacatgctgg tcatcctcat cgtgatgtga taaactgcaa aaggctgaag      60
agcatgactg acatctacct gctc                                             84

<210> SEQ ID NO 47
<211> LENGTH: 83
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 47
ttttgtgggc aacatgctgg tcatcctcat cctgactgat aaactgcaaa aggctgaaga      60
gcatgactga catctacctg ctc                                              83

<210> SEQ ID NO 48
<211> LENGTH: 81
<212> TYPE: DNA
<213> ORGANISM: Artificial Sequence
<220> FEATURE:
<223> OTHER INFORMATION: human CCR-5 gene sequence with ZFN-mediated
      mutation
```

```
<400> SEQUENCE: 48
ttttgtgggc aacatgctgg tcatcctcat cctgataaaa actgcaaaag gctgaagagc      60
atgactgaca tctacctgct c                                               81

<210> SEQ ID NO 49
<211> LENGTH: 80
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 49
ttttgtgggc aacatgctgg tcatcctcat cctgataaaa ctgcaaaagg ctgaagagca      60
tgactgacat ctacctgctc                                                 80

<210> SEQ ID NO 50
<211> LENGTH: 81
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 50
ttttgtgggc aacatgctgg tcatcctcat cctgatataa actgcaaaag gctgaagagc      60
atgactgaca tctacctgct c                                               81

<210> SEQ ID NO 51
<211> LENGTH: 125
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 51
ttttgtgggt aacatgctgg tcatcctcat ctagatcagt gagtatgccc tgatggcgtc      60
tggactggat gcctcgccta gaaaactgca aaaggctgaa gagcatgact gacatctacc    120
tgctc                                                                125

<210> SEQ ID NO 52
<211> LENGTH: 130
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 52
ttttgtgggc aacatgctgg tcatcctcat ccttctagat cagtgagtat gccctgatgg      60
cgtctggact ggatgcctcg tctagataaa ctgcaaaagg ctgaagagca tgactgacat    120
ctacctgctc                                                           130

<210> SEQ ID NO 53
<211> LENGTH: 210
<212> TYPE: DNA
<213> ORGANISM: Artificial Sequence
<220> FEATURE:
<223> OTHER INFORMATION: human CCR-5 gene sequence with ZFN-mediated
      mutation
```

<400> SEQUENCE: 53
ttttgtgggc aacatgctgg tcatcctcat cctgatgccc ctgcaggtcg caccacagag     60
ctcacccaac ctgagtccct ctggtactga ccactccaga ctgagtccct ctggtactga    120
ccactccgga ctgagtccct ctggtactga ccactcaggg ctctgataaa ctgcaaaagg    180
ctgaagagca tgactgacat ctacctgctc                                     210

<210> SEQ ID NO 54
<211> LENGTH: 64
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 54
ttttgtgggc aacatgctgg tcatcagcaa aaggctgaag agcatgactg acatctacct     60
gctc                                                                  64

<210> SEQ ID NO 55
<211> LENGTH: 62
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 55
ttttgtgggc aacatgctgg tcatcctcaa ggctgaagag catgactgac atctacctgc     60
tc                                                                    62

<210> SEQ ID NO 56
<211> LENGTH: 73
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 56
ttttgtgggc aacatgctgg tcatcctcat aaactgcaaa aggctgaaga gcatgactga     60
catctacctg ctc                                                        73

<210> SEQ ID NO 57
<211> LENGTH: 76
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 57
ttttgtgggc aacatgctgg tcatcctcat cctaaactgc aaaaggctga agagcatgac     60
tgacatctac ctgctc                                                     76

<210> SEQ ID NO 58
<211> LENGTH: 71
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 58

```
ttttgtgggc aacatgctgg tcatcctcat cctgcaaaag gctgaagagc atgactgaca    60
tctacctgct c                                                        71
```

<210> SEQ ID NO 59
<211> LENGTH: 77
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 59

```
ttttgtgggc aacatgctgg tcatcctcat cctgaaactg caaaaggctg aagagcatga    60
ctgacatcta cctgctc                                                  77
```

<210> SEQ ID NO 60
<211> LENGTH: 78
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 60

```
ttttgtgggc aacatgctgg tcatcctcat cctgaaaact gcaaaaggct gaagagcatg    60
actgacatct acctgctc                                                 78
```

<210> SEQ ID NO 61
<211> LENGTH: 63
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 61

```
ttttgtgggc aacatgctgg tcatcctcat cctgacaaga gcatgactga catctacctg    60
ctc                                                                 63
```

<210> SEQ ID NO 62
<211> LENGTH: 62
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 62

```
ttttgtgggc aacatgctgg tcatcctcat cctgatagag catgactgac atctacctgc    60
tc                                                                  62
```

<210> SEQ ID NO 63
<211> LENGTH: 72
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 63

```
ttttgtgggc aacatgctgg tcatcctcat cctgataaaa ggctgaagag catgactgac    60
atctacctgc tc                                                       72
```

<210> SEQ ID NO 64
<211> LENGTH: 66
<212> TYPE: DNA
<213> ORGANISM: Artificial Sequence
<220> FEATURE:
<223> OTHER INFORMATION: human CCR-5 gene sequence with ZFN-mediated mutation

<400> SEQUENCE: 64
ttttgtgggc aacatgctgg tcatcctcat cctgatatga agagcatgac tgacatctac    60
ctgctc    66

<210> SEQ ID NO 65
<211> LENGTH: 78
<212> TYPE: DNA
<213> ORGANISM: Artificial Sequence
<220> FEATURE:
<223> OTHER INFORMATION: human CCR-5 gene sequence with ZFN-mediated mutation

<400> SEQUENCE: 65
ttttgtgggc aacatgctgg tcatcctcat cctgataact gcaaaaggct gaagagcatg    60
actgacatct acctgctc    78

<210> SEQ ID NO 66
<211> LENGTH: 71
<212> TYPE: DNA
<213> ORGANISM: Artificial Sequence
<220> FEATURE:
<223> OTHER INFORMATION: human CCR-5 gene sequence with ZFN-mediated mutation

<400> SEQUENCE: 66
ttttgtgggc aacatgctgg tcatcctcat cctgataaag gctgaagagc atgactgaca    60
tctacctgct c    71

<210> SEQ ID NO 67
<211> LENGTH: 75
<212> TYPE: DNA
<213> ORGANISM: Homo sapiens

<400> SEQUENCE: 67
atctttggtt ttgtgggcaa catgctggtc atcctcatcc tgataaactg caaaaggctg    60
aagagcatga ctgac    75

<210> SEQ ID NO 68
<211> LENGTH: 75
<212> TYPE: DNA
<213> ORGANISM: Homo sapiens

<400> SEQUENCE: 68
gtcagtcatg ctcttcagcc ttttgcagtt tatcaggatg aggatgacca gcatgttgcc    60
cacaaaacca aagat    75

<210> SEQ ID NO 69
<211> LENGTH: 78
<212> TYPE: DNA
<213> ORGANISM: Artificial Sequence
<220> FEATURE:
<223> OTHER INFORMATION: Human CCR-5 gene sequence with ZFN-mediated mutation

<400> SEQUENCE: 69

-continued ttttgtgggc aacatgctgg tcatcctcat ctgataaact gcaaaaggct gaagagcatg    60
actgacatct acctgctc                                                  78

<210> SEQ ID NO 70
<211> LENGTH: 77
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 70
ttttgtgggc aacatgctgg tcatcctcat ccttaaactg caaaaggctg aagagcatga    60
ctgacatcta cctgctc                                                   77

<210> SEQ ID NO 71
<211> LENGTH: 84
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 71
ttttgtgggc aacatgctgg tcatcctcat cctgatctga taaactgcaa aaggctgaag    60
agcatgactg acatctacct gctc                                           84

<210> SEQ ID NO 72
<211> LENGTH: 82
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 72
ttttgtgggc aacatgctgg tcatcctcat cctgatgata aactgcaaaa ggctgaagag    60
catgactgac atctacctgc tc                                             82

<210> SEQ ID NO 73
<211> LENGTH: 77
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 73
ttttgtgggc aacatgctgg tcatcctcat cgataaactg caaaaggctg aagagcatga    60
ctgacatcta cctgctc                                                   77

<210> SEQ ID NO 74
<211> LENGTH: 77
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 74
ttttgtgggc aacatgctgg tcatcctcac tgataaactg caaaaggctg aagagcatga    60
ctgacatcta cctgctc                                                   77

```
<210> SEQ ID NO 75
<211> LENGTH: 76
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 75
ttttgtgggc aacatgctgg tcatcctcat cataaactgc aaaaggctga agagcatgac    60
tgacatctac ctgctc                                                   76

<210> SEQ ID NO 76
<211> LENGTH: 75
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 76
ttttgtgggc aacatgctgg tcatcctcat ctaaactgca aaaggctgaa gagcatgact    60
gacatctacc tgctc                                                    75

<210> SEQ ID NO 77
<211> LENGTH: 75
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 77
ttttgtgggc aacatgctgg tcatcctcat ccaaactgca aaaggctgaa gagcatgact    60
gacatctacc tgctc                                                    75

<210> SEQ ID NO 78
<211> LENGTH: 74
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 78
ttttgtgggc aacatgctgg tcatcctcat caaactgcaa aaggctgaag agcatgactg    60
acatctacct gctc                                                     74

<210> SEQ ID NO 79
<211> LENGTH: 79
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 79
ttttgtggac aacatgctgg tcatcctcat cctgataaac tgcaaaaggc tgaagagcat    60
gactgacatc tacctgctc                                                79

<210> SEQ ID NO 80
<211> LENGTH: 79
<212> TYPE: DNA
<213> ORGANISM: Homo sapiens
```

-continued

```
<400> SEQUENCE: 80
ttttgtgggc aacatgctgg tcatcctcat cctgataaac tgcaaaaggc tgaagagcat      60
gactgacatc tacctgctc                                                  79

<210> SEQ ID NO 81
<211> LENGTH: 79
<212> TYPE: DNA
<213> ORGANISM: Artificial Sequence
<220> FEATURE:
<223> OTHER INFORMATION: human CCR-5 gene sequence with ZFN-mediated
      mutation

<400> SEQUENCE: 81
ttttgtgggc aacatgctgg tcatcctcat cgtggtaaac tgcaaaaggc tgaagagcat      60
gactgacatc tacctgctc                                                  79

<210> SEQ ID NO 82
<211> LENGTH: 79
<212> TYPE: DNA
<213> ORGANISM: Artificial Sequence
<220> FEATURE:
<223> OTHER INFORMATION: human CCR-5 gene sequence with ZFN-mediated
      mutation
<220> FEATURE:
<221> NAME/KEY: misc_feature
<222> LOCATION: (32)..(32)
<223> OTHER INFORMATION: n is a, c, g, or t

<400> SEQUENCE: 82
ttttgtgggc aacatgctgg tcatcctcat cntgataaac tgcaaaaggc tgaagagcat      60
gactgacatc tacctgctc                                                  79

<210> SEQ ID NO 83
<211> LENGTH: 79
<212> TYPE: DNA
<213> ORGANISM: Artificial Sequence
<220> FEATURE:
<223> OTHER INFORMATION: human CCR-5 gene sequence with ZFN-mediated
      mutation
<220> FEATURE:
<221> NAME/KEY: misc_feature
<222> LOCATION: (17)..(17)
<223> OTHER INFORMATION: n is a, c, g, or t

<400> SEQUENCE: 83
ttttgtgggc aacatgntgg tcatcctcat cctgataaac tgcaaaaggc tgaagagcat      60
gactgacatc tacctgctc                                                  79

<210> SEQ ID NO 84
<211> LENGTH: 74
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 84
ttttgtgggc aacatgctgg tcatcctcaa taaactgcaa aaggctgaag agcatgactg      60
acatctacct gctc                                                       74

<210> SEQ ID NO 85
<211> LENGTH: 72
<212> TYPE: DNA
<213> ORGANISM: Artificial Sequence
<220> FEATURE:
```

```
-continued

<223> OTHER INFORMATION: Human CCR-5 gene sequence with ZFN-mediated
      mutation

<400> SEQUENCE: 85
ttttgtgggc aacatgctgg tcatctgata aactgcaaaa ggctgaagag catgactgac      60
atctacctgc tc                                                         72

<210> SEQ ID NO 86
<211> LENGTH: 72
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 86
ttttgtgggc aacatgctgg tcatccgata aactgcaaaa ggctgaagag catgactgac      60
atctacctgc tc                                                         72

<210> SEQ ID NO 87
<211> LENGTH: 69
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 87
ttttgtgggc aacatgctgg tttgataaac tgcaaaaggc tgaagagcat gactgacatc      60
tacctgctc                                                             69

<210> SEQ ID NO 88
<211> LENGTH: 71
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 88
ttttgtgggc aacatgctgg tcatcgataa actgcaaaag gctgaagagc atgactgaca      60
tctacctgct c                                                          71

<210> SEQ ID NO 89
<211> LENGTH: 70
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 89
ttttgtgggc aacatgctgg tcatcctcaa ctgcaaaagg ctgaagagca tgactgacat      60
ctacctgctc                                                            70

<210> SEQ ID NO 90
<211> LENGTH: 74
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 90
```

```
ttttgtgggc aacatgctgg tcatcctcat cctgatgcaa aaggctgaag agcatgactg    60
acatctacct gctc                                                     74
```

```
<210> SEQ ID NO 91
<211> LENGTH: 68
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 91
ttttgtgggc aacatgctgg tcatcctcat ccaaaaggct gaagagcatg actgacatct    60
acctgctc                                                            68
```

```
<210> SEQ ID NO 92
<211> LENGTH: 61
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 92
ttttgtgggc aacatgctgg tcatcctcat cctgaagagc atgactgaca tctacctgct    60
c                                                                   61
```

```
<210> SEQ ID NO 93
<211> LENGTH: 59
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 93
ttttgtaggc aacatgctgg tcatcctcac tgaagagcat gactgacatc tacctgctc    59
```

```
<210> SEQ ID NO 94
<211> LENGTH: 60
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 94
ttttgtgggc aacatgctga ctgcaaaagg ctgaagagca tgactgacat ctacctgctc    60
```

```
<210> SEQ ID NO 95
<211> LENGTH: 62
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 95
ttttgtgggc aacatgcgta aactgcaaaa ggctgaagag catgactgac atctacctgc    60
tc                                                                  62
```

```
<210> SEQ ID NO 96
<211> LENGTH: 63
<212> TYPE: DNA
<213> ORGANISM: Artificial Sequence
```

-continued

```
<220> FEATURE:
<223> OTHER INFORMATION: Human CCR-5 gene sequence with ZFN-mediated
      mutation

<400> SEQUENCE: 96
ttttgtgggc aacatgtgat aaactgcaaa aggctgaaga gcatgactga catctacctg    60
ctc                                                                  63

<210> SEQ ID NO 97
<211> LENGTH: 66
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 97
ttttgtgggc aacatgctgg tctaaactgc aaaaggctga agagcatgac tgacatctac    60
ctgctc                                                               66

<210> SEQ ID NO 98
<211> LENGTH: 58
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 98
ttttgtgggc aacatgctgg tcaaaaggct gaagagcatg actgacatct acctgctc      58

<210> SEQ ID NO 99
<211> LENGTH: 53
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 99
ttttgtgggc aacatgcaaa aggctgaaga gcatgactga catctacctg ctc           53

<210> SEQ ID NO 100
<211> LENGTH: 43
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 100
ttttgtgggc aacatgaaga gcatgactga catctacctg ctc                      43

<210> SEQ ID NO 101
<211> LENGTH: 36
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 101
ttttgtgggc aacatatgac tgacatctac ctgctc                              36

<210> SEQ ID NO 102
<211> LENGTH: 79
```

<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 102
ttttgtgggc aacatgctgg tcatcctcat cctgatataa actgcaaaag gctgaagagc    60
atgactgaca tctacctgc                                                 79

<210> SEQ ID NO 103
<211> LENGTH: 79
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 103
ttttgtgggc aacatgctgg tcatcctcat cctgataaaa actgcaaaag gctgaagagc    60
atgactgaca tctacctgc                                                 79

<210> SEQ ID NO 104
<211> LENGTH: 79
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 104
ttttgtgggc aacatgctgg tcatcctcat cctgatgata aactgcaaaa ggctgaagag    60
catgactgac atctacctg                                                 79

<210> SEQ ID NO 105
<211> LENGTH: 79
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 105
ttttgtgggc aacatgctgg tcatcctcat cctgactgat aaactgcaaa aggctgaaga    60
gcatgactga catctacct                                                 79

<210> SEQ ID NO 106
<211> LENGTH: 79
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 106
ttttgtgggc aacatgctgg tcatcctcat cctgattgat aaactgcaaa aggctgaaga    60
gcatgactga catctacct                                                 79

<210> SEQ ID NO 107
<211> LENGTH: 79
<212> TYPE: DNA
<213> ORGANISM: Artificial Sequence
<220> FEATURE:
<223> OTHER INFORMATION: Human CCR-5 gene sequence with ZFN-mediated
      mutation

```
<400> SEQUENCE: 107
ttttgtgggc aacatgctgg tcatcctcat cctgatctga taaactgcaa aaggctgaag        60
agcatgactg acatctacc                                                    79

<210> SEQ ID NO 108
<211> LENGTH: 79
<212> TYPE: DNA
<213> ORGANISM: Artificial Sequence
<220> FEATURE:
<223> OTHER INFORMATION: Human CCR-5 gene sequence with ZFN-mediated
      mutation

<400> SEQUENCE: 108
ttttgtgggc aacatgctgg tcatcctcat cttaatttaa taaactgcaa aaggctgaag        60
agcatgactg acatctacc                                                    79
```

METHODS AND COMPOSITIONS FOR GENE INACTIVATION

CROSS-REFERENCE TO RELATED APPLICATIONS

The present application is a continuation of U.S. patent application Ser. No. 11/805,707, filed May 23, 2007, now U.S. Pat. No. 7,951,925 which claims the benefit of U.S. Provisional Application No. 60/808,501, filed May 25, 2006; U.S. Provisional Application No. 60/847,269, filed Sep. 26, 2006 and U.S. Provisional Application No. 60/926,911, filed Apr. 30, 2007, all of which disclosures are hereby incorporated by reference in their entireties herein.

STATEMENT OF RIGHTS TO INVENTIONS MADE UNDER FEDERALLY SPONSORED RESEARCH

Not applicable.

TECHNICAL FIELD

The present disclosure is in the fields of polypeptide and genome engineering and homologous recombination.

BACKGROUND

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; 20060188987; and International Patent Publication WO 07/014,275, the disclosures of which are incorporated by reference in their entireties for all purposes.

CCR5, a 7-transmembrane chemokine receptor, is the major co-receptor for HIV-1 entry into CD4 T cells (Samson et al. (1996) *Nature* 382:722-725; Deng et al. (1996) *Nature* 381:661-666; Alkhatib (1996) *Science* 272:1955-1958). Since the discovery of the HIV-1 resistance conferring homozygous Δ32 deletion in the CCR5 gene, CCR5 has been intensively studied as a prime target for HIV therapy. Although small molecules have been shown to induce receptor internalization or block CCR5-HIV interaction (Fatkenheuer et al. (2005) *Nat. Med.* 11:1170-1172), these small molecule approaches have resulted in the development of resistance via selection for escape mutants which interestingly continue to use CCR5 for viral entry (Kuhmann et al. (2004) *J. Virol.* 78:2790-2807). Similarly, intrabody, antisense and RNAi-based approaches have to date only partially blocked CCR5 expression.

Thus, there remains a need for compositions that completely knock-out CCR5 for phenotypic penetrance and long-term resistance to HIV infection.

SUMMARY

Disclosed herein are compositions and methods for partial or complete inactivation of a target gene. Also disclosed are methods of making and using these compositions (reagents), for example to inactivate a gene in a cell for therapeutic purposes and/or to produce cell lines in which a target gene is inactivated.

In one aspect, provided herein are zinc finger nucleases (ZFNs) that have target sites in the human CCR-5 gene. In some embodiments, cleavage within the CCR-5 gene with these nucleases results in permanent disruption (e.g., mutation) of the CCR5 gene. In certain embodiments, the zinc finger domain(s) is(are) engineered to bind to a target site upstream of the naturally occurring CCR5 Δ32 mutation. The zinc finger proteins may include 1, 2, 3, 4, 5, 6 or more zinc fingers, each zinc finger having a recognition helix that binds to a target subsite in the target gene. In certain embodiments, the target gene is CCR-5 and the zinc finger proteins comprise 4 fingers (designated F1, F2, F3 and F4 and ordered F1 to F4 from N-terminus to C-terminus) and comprise the amino acid sequence of the recognition regions shown in Table 1.

Thus, in certain aspects, provided herein is a protein comprising an engineered zinc finger protein DNA-binding domain, wherein the DNA-binding domain comprises four zinc finger recognition regions ordered F1 to F4 from N-terminus to C-terminus, and wherein F1, F3, and F4 comprise the following amino acid sequences: DRSNLSR (SEQ ID NO:2); F3: RSDNLAR (SEQ ID NO:4); and F4: TSGNLTR (SEQ ID NO:8). In certain embodiments, F2 comprises the amino acid sequence ISSNLNS (SEQ ID NO:5). Alternatively, F2 comprises the amino acid sequence VSSNLTS (SEQ ID NO:6).

Any of the proteins described herein may further comprise a cleavage domain and/or a cleavage half-domain (e.g., a wild-type or engineered FokI cleavage half-domain). Thus, in any of the ZFNs described herein, the nuclease domain may comprise a wild-type nuclease domain or nuclease half-domain (e.g., a FokI cleavage half domain). In other embodiments, the ZFNs comprise engineered nuclease domains or half-domains, for example engineered FokI cleavage half domains that form obligate heterodimers. See, e.g., U.S. Provisional Patent Application No. 60/808,486, filed May 25, 2006.

In another aspect, the disclosure provides a polynucleotide encoding any of the proteins described herein. Any of the polynucleotides described herein may also comprise sequences (donor or patch sequences) for targeted insertion into the target gene (e.g., CCR-5).

In yet another aspect, a gene delivery vector comprising any of the polynucleotides described herein is provided. In certain embodiments, the vector is an adenovirus vector (e.g., an Ad5/35 vector). Thus, also provided herein are adenovirus (Ad) vectors comprising a sequence encoding at least one zinc finger nuclease (ZFN) and/or a donor sequence for targeted integration into a target gene. In certain embodiments, the Ad vector is a chimeric Ad vector, for example an Ad5/35 vector. In additional embodiments, the target gene is the human CCR-5 gene. The vectors described herein may comprise donor sequences. In certain embodiments, a single vector comprises sequences encoding one or more ZFNs and the donor sequence(s). In other embodiments, the donor sequence(s) are contained in a first vector and the ZFN-encoding sequences are present in a second vector.

The ZFN-sequences of the vectors (e.g., Ad vectors) described herein will typically encode a fusion of a zinc finger protein (ZFP) and a cleavage domain or cleavage half-domain (i.e., a nuclease domain). The zinc finger protein portion of the ZFN is engineered to bind to a target site in the target gene. Zinc finger proteins may include 1, 2, 3, 4, 5, 6 or more zinc fingers, each zinc finger having a recognition helix that binds to a target subsite in the target gene. In certain embodiments, the target gene is CCR-5 and the zinc finger proteins comprise 4 fingers (designated F1, F2, F3 and F4) and comprise the amino acid sequence of the recognition regions shown in Table 1.

In any of the polynucleotides or proteins described herein, the cleavage domain may comprise at least one cleavage domain or at least one cleavage half-domain. In certain embodiments, the cleavage domain or cleavage half-domain is a wild-type cleavage domain (e.g., a FokI wild-type cleavage half-domain). In other embodiments, the cleavage domain or cleavage half-domain is engineered.

In yet another aspect, the disclosure provides an isolated cell comprising any of the proteins, polynucleotides and/or vectors described herein. In certain embodiments, the cell is selected from the group consisting of a hematopoietic stem cell, a T-cell (e.g., CD4$^+$ T-cell), a macrophage, a dendritic cell and an antigen-presenting cell. In another aspect, cells comprising one or more Ad vectors as described herein (Ad-ZFN, Ad-ZFN-donor and/or Ad-donor vectors) are also described. Cells include, for example, peripheral Blood Mononuclear Cells (PBMCs), macrophages, mesenchymal stem cells, human embryonic stem cells (hES cells), hematopoietic stem cell (e.g., CD34$^+$ cells), T-cells (e.g., CD4$^+$ cells), dendritic cells or antigen-presenting cells; or a cell line such as K562 (chronic myelogenous leukemia), HEK293 (embryonic kidney), PM-1 (CD4$^+$ T-cell), THP-1 (monocytic leukemia) or GHOST (osteosarcoma).

In another aspect, described herein are methods of inactivating a target gene in a cell by introducing one or more proteins, polynucleotides and/or vectors into the cell as described herein. In any of the methods described herein the ZFNs may induce targeted mutagenesis, targeted deletions of cellular DNA sequences, and/or facilitate targeted recombination at a predetermined chromosomal locus. Thus, in certain embodiments, the ZFNs delete one or more nucleotides of the target gene. In other embodiments, a genomic sequence in the target gene is replaced, for example using an Ad-ZFN as described herein and a "donor" sequence that is inserted into the gene following targeted cleavage with the ZFN. The donor sequence may be present in the Ad-ZFN vector, present in a separate Ad vector or, alternatively, may be introduced into the cell using a different nucleic acid delivery mechanism. In certain embodiments, the target gene is a CCR-5 gene.

In another aspect, methods of using the zinc finger proteins and fusions thereof for mutating the CCR-5 gene and/or inactivating CCR-5 function in a cell or cell line are provided. Thus, a method for inactivating a CCR-5 gene in a human cell is provided, the method comprising administering to the cell any of the proteins or polynucleotides described herein.

In yet another aspect, the disclosure provides a method for treating or preventing HIV infection in a subject, the method comprising: (a) introducing, into a cell, a first nucleic acid encoding a first polypeptide, wherein the first polypeptide comprises: (i) a zinc finger DNA-binding domain that is engineered to bind to a first target site in the CCR5 gene; and (ii) a cleavage domain; under conditions such that the polypeptide is expressed in the cell, whereby the polypeptide binds to the target site and cleaves the CCR5 gene; and (b) introducing the cell into the subject. In certain embodiments, the cell is selected from the group consisting of a hematopoietic stem cell, a T-cell, a macrophage; a dendritic cell and an antigen-presenting cell. The nucleic acid may comprise any of the polynucleotides described herein. In any of the methods, the first nucleic acid may further encode a second polypeptide, wherein the second polypeptide comprises: (i) a zinc finger DNA-binding domain that is engineered to bind to a second target site in the CCR5 gene; and (ii) a cleavage domain; such that the second polypeptide is expressed in the cell, whereby the first and second polypeptides bind to their respective target sites and cleave the CCR5 gene. Similarly, any of these methods may further comprise the step of introducing into the cell a second nucleic acid, wherein the second nucleic acid contains two regions of homology to the CCR-5 gene, flanking a sequence that is non-homologous to the CCR-5 gene.

In any of the methods and compositions described herein, the cell can be, for example, a hematopoietic stem cell (e.g., a CD34$^+$ cell), a T-cell (e.g., a CD4$^+$ cell), a macrophage, a dendritic cell or an antigen-presenting cell; or a cell line such as K562 (chronic myelogenous leukemia), HEK293 (embryonic kidney), PM-1 (CD4$^+$ T-cell), THP-1 (monocytic leukemia) or GHOST (osteosarcoma).

Furthermore, any of the methods described herein can be practiced in vitro, in vivo and/or ex vivo. In certain embodiments, the methods are practiced ex vivo, for example to modify PBMCs, e.g., T-cells, to make them resistant to HIV infection via disruption of CCR-5.

BRIEF DESCRIPTION OF THE DRAWINGS

FIG. 2 shows the amino acid sequence of the wild-type FokI cleavage half-domain (SEQ ID NO:33). Positions at which the sequence can be altered (486, 490, 499 and 538) to form engineered cleavage half-domains are bolded and underlined.

FIG. 3 shows the amino acid sequence of an exemplary engineered cleavage half-domain (SEQ ID NO:34) that forms a heterodimer with the engineered cleavage half-domain shown in FIG. 4. Positions at which the sequence was altered as compared to wild-type (corresponding to amino acid residues 486 and 499) are underlined.

FIG. 4 shows the amino acid sequence of another exemplary engineered cleavage half-domain (SEQ ID NO:35) that can be used in the ZFNs described herein. Positions at which the sequence was altered as compared to wild-type (corresponding to amino acid residues 490 and 538) are underlined.

FIG. 5 shows the nucleotide sequence of portion of a CCR-5 gene (SEQ ID NO:36) used to make a donor (patch) sequence having CCR-5 homology arms. See also Example 1.

FIG. 6 shows the nucleotide sequence of a 47 bp "patch" sequence (SEQ ID NO:37) used for insertion into the CCR-5 gene. See also Example 1.

FIG. 7 shows the nucleotide sequence of the donor sequence (SEQ ID NO:38) used for targeted insertion into the CCR-5 gene. The 5' CCR-5 homology arm corresponds to nucleotides 1-471; the "patch" sequence for targeted insertion into CCR-5 is underlined and corresponds to nucleotides 472-518; and the 3' CCR-5 homology arm corresponds to nucleotides 519-1928. See also Example 1.

FIG. 8 depicts sequences (SEQ ID NOS: 54-66) of a portion of the CCR-5 gene in cells transduced with Ad5/35-ZFN. Cell type is shown in Column 3. Missing bases as compared to wild-type CCR-5 sequence are denoted with a period.

FIG. 9 (SEQ ID NOS: 43, 44, 46-50) depicts sequence analysis of a portion of the CCR-5 gene in cells transduced with an Ad5/35-ZFN. Cell type is indicated in Column 3. The modified genomes shown in this figure had various small insertions (underlined bases) in the CCR-5 gene and, in one case, a deletion, indicated by a period.

FIG. 10 (SEQ ID NOS: 51-53) depicts sequence analysis of a portion of the CCR-5 gene in cells transduced with an Ad5/35-ZFN. The modified genomes shown in this Figure had various longer insertions (underlined bases) in the CCR-5 gene.

FIG. 14, panels A and B, are graphs depicting flow cytometry measurements of CCR5 surface expression (FIG. 14A) or GFP expression (FIG. 14B) of GHOST-CCR5 cells transduced with an Ad5/35 vector encoding ZFN 215 or ZFN 224.

FIG. 16 shows sequences of CCR5 alleles in ZFN-treated PM1 cells at day 52 post-HIV challenge.

FIG. 17 shows levels of ZFN-disrupted CCR5 alleles in primary CD4 T cells from an anonymous healthy donor transduced with an Ad5/35 vector expressing CCR5-ZFN215, CCR5-ZFN224, or GFP; at MOIs of 30 or 100, as determined by Surveyor™ nuclease assay. Bands corresponding to disrupted CCR5 alleles are indicated by arrows. The percentage of disrupted CCR5 alleles is indicated below each lane.

FIG. 18 depicts the population doubling rate for CD4 T cells transduced with Ad5/35 vectors whose genomes encoded either CCR5-ZFNs or GFP (control cells). Cells were transduced with the Ad5/35 vectors on day 0. The line connecting points shown by triangles depicts doubling rates of non-transduced cells; the line connecting points shown by squares depicts doubling rates of Ad5/35 CCR5 ZFN 224-transduced cells; and the line connecting points shown by diamonds depicts doubling rates of Ad5/35 GFP transduced cells.

DETAILED DESCRIPTION

Figure 1:
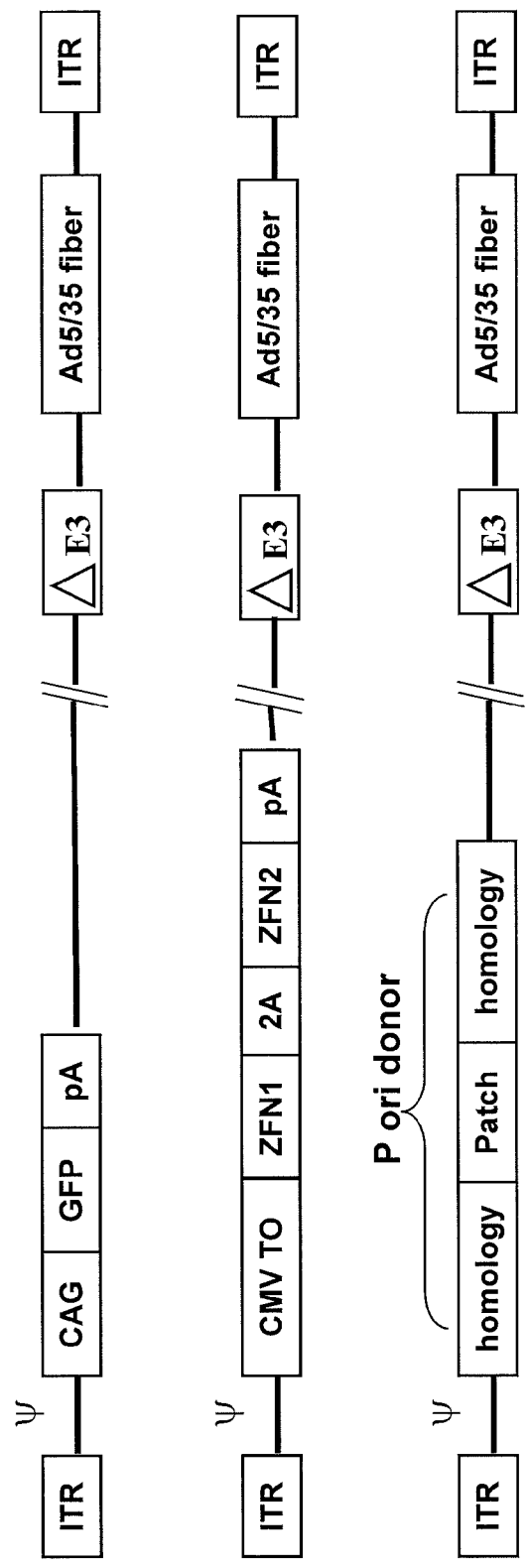
FIG. 1 shows schematic diagrams of the Ad5/35 vectors in which sequences encoding E1 are deleted and replaced with a transgene expression cassette (e.g., encoding GFP, ZFNs and/or donor sequences).

Disclosed herein are zinc finger nuclease (ZFNs) targeting the human CCR5 gene (CCR5-ZFNs). These ZFNs efficiently generate a double strand break (DSB), for example at a predetermined site in the CCR5 coding region. The site can be, for example, upstream of the CCR5Δ32 mutation. Transient expression of the ZFNs described herein promotes highly efficient and permanent disruption of the CCR5 gene in human cells, including primary human CD4 T lymphocytes, confers robust protection against HIV-1 infection and provides a powerful selective advantage to these cells both in vitro and in vivo.

In particular, transient delivery of CCR5-ZFNs results in the permanent disruption of the human CCR5 gene with efficiencies surpassing 50% in primary human CD4 T cells. CCR5-ZFN action is highly specific and well tolerated, as revealed by (i) examination of the stability, growth and engraftment characteristics of the ZFN-modified sub-population even in the absence of selection, (ii) direct staining for intranuclear DSB-induced 53BP1 foci, and (iii) testing for cleavage at the most similar putative off-target genomic sites. Moreover, in the presence of a selective pressure in the form of active HIV-1 infection, ZFN-modification confers a profound survival advantage during CCR5-tropic (but not CXCR4-tropic) HIV-1 challenge assays in vitro to levels comparable to those obtained with homozygous CCR5Δ32 cells.

CCR5-ZFN-mediated genome editing as described herein may be employed to generate a CCR5 null genotype in primary human cells. Moreover, as expected for a genetically determined trait, the ZFN-modified cells demonstrated stable and heritable resistance to HIV-1 infection both in vitro and in vivo.

Small molecule, intrabody, and anti-sense or RNAi-based approaches to HIV treatment via CCR5 disruption incompletely repress or block CCR5 at the mRNA or protein level. See, Levine et al. (2006) Proc. Nat'l Acad. Sci. USA 103: 17372-17377; Trkola et al. (2002) Proc. Nat'l Acad. Sci. USA 99:395-400). Thus, unlike other approaches, the CCR5-ZFNs described herein generate a true CCR5 null cell, which, like the naturally selected CCR5Δ32, is permanently and completely CCR5 negative, preferentially survives HIV-1 infection, and gives rise to daughter cells that are equally resilient to HIV-1 infection. Permanent genetic modification by CCR5-ZFNs blocks viral entry without the requirement for the integration of any foreign DNA into the genome, as transient ZFN gene delivery and expression is sufficient to eliminate CCR5 expression.

Also disclosed herein are adenovirus (Ad) vectors comprising ZFNs and/or donor sequences and cells comprising these Ad vectors. These Ad vectors are useful in methods for targeted cleavage of cellular chromatin and for targeted alteration of a cellular nucleotide sequence, e.g., by targeted cleavage followed by non-homologous end joining or by targeted cleavage followed by homologous recombination between an exogenous polynucleotide (comprising one or more regions of homology with the cellular nucleotide sequence) and a genomic sequence.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff =60; expect=10; Matrix=BLOSUM62; Descriptions=50 sequences; sort by=HIGH SCORE; Databases=non-redundant, GenBank+ EMBL+DDBJ+PDB+GenBank CDS translations+Swiss protein+Spupdate+PIR. Details of these programs can be found at the following internet address: http://www.ncbi.nlm.nih.gov/cgi-bin/BLAST. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

An "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 20050064474 and 20060188987 and U.S. Provisional Application No. 60/808,486 (filed May 25, 2006), incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid.

Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eucaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Zinc Finger Nucleases

Described herein are zinc finger nucleases (ZFNs) that can be used for gene inactivation, for example inactivation of the CCR5 gene. ZFNs comprise a zinc finger protein (ZFP) and a nuclease (cleavage) domain.

A. Zinc Finger Proteins

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in related to U.S. Publication Nos. 20030232410; 20050208489; 2005064474; 20050026157; 20060188987; International Publication WO 07/014,275; U.S. patent application Ser. Nos. 10/587,723 (filed Jul. 27, 2006); 11/493,423 (filed Jul. 26, 2006), the disclosures of which are incorporated by reference in their entireties for all purposes.

In certain embodiments, the zinc finger nucleases of the Ad-ZFN vectors described herein bind in a CCR-5 gene. Table 1 describes a number of zinc finger binding domains that have been engineered to bind to nucleotide sequences in the human CCR-5 gene. Each row describes a separate zinc finger DNA-binding domain. The DNA target sequence for each domain is shown in the first column (DNA target sites indicated in uppercase letters; non-contacted nucleotides indicated in lowercase), and the second through fifth columns show the amino acid sequence of the recognition region (amino acids −1 through +6, with respect to the start of the helix) of each of the zinc fingers (F1 through F4) in the protein. Also provided in the first column is an identification number for each protein.

TABLE 1

Zinc finger nucleases targeted to the human CCR-5 gene

| Target sequence | F1 | F2 | F3 | F4 |
|---|---|---|---|---|
| r162 designs | | | | |
| GATGAGGATGAC (SEQ ID NO: 1) 7296 | DRSNLSR (SEQ ID NO: 2) | TSANLSR (SEQ ID NO: 3) | RSDNLAR (SEQ ID NO: 4) | TSANLSR (SEQ ID NO: 3) |
| GATGAGGATGAC (SEQ ID NO: 1) 8181 | DRSNLSR (SEQ ID NO: 2) | ISSNLNS (SEQ ID NO: 5) | RSDNLAR (SEQ ID NO: 4) | TSANLSR (SEQ ID NO: 3) |
| GATGAGGATGAC (SEQ ID NO: 1) 8182 | DRSNLSR (SEQ ID NO: 2) | VSSNLTS (SEQ ID NO: 6) | RSDNLAR (SEQ ID NO: 4) | TSANLSR (SEQ ID NO: 3) |
| GATGAGGATGAC (SEQ ID NO: 1) 8262 | DRSNLSR (SEQ ID NO: 2) | ISSNLNS (SEQ ID NO: 5) | RSDNLAR (SEQ ID NO: 4) | NRDNLSR (SEQ ID NO: 7) |
| GATGAGGATGAC (SEQ ID NO: 1) 8266 | DRSNLSR (SEQ ID NO: 2) | ISSNLNS (SEQ ID NO: 5) | RSDNLAR (SEQ ID NO: 4) | TSGNLTR (SEQ ID NO: 8) |
| GATGAGGATGAC (SEQ ID NO: 1) 8267 | DRSNLSR (SEQ ID NO: 2) | VSSNLTS (SEQ ID NO: 6) | RSDNLAR (SEQ ID NO: 4) | TSGNLTR (SEQ ID NO: 8) |
| GATGAGGATGAC (SEQ ID NO: 1) 7741 | DRSNLSR (SEQ ID NO: 2) | TSGNLTR (SEQ ID NO: 8) | RSDNLAR (SEQ ID NO: 4) | TSGNLTR (SEQ ID NO: 8) |
| 168 designs | | | | |
| AAACTGCAAAAG (SEQ ID NO: 9) 7745 | RSDNLSV (SEQ ID NO: 10) | QNANRIT (SEQ ID NO: 11) | RSDVLSE (SEQ ID NO: 12) | QRNHRTT (SEQ ID NO: 13) |
| AAACTGCAAAAG (SEQ ID NO: 9) 8165 | RSDNLSN (SEQ ID NO: 14) | QNANRIT (SEQ ID NO: 11) | RSDVLSE (SEQ ID NO: 12) | QRNHRTT (SEQ ID NO: 13) |
| AAACTGCAAAAG (SEQ ID NO: 9) 8191 | RSDNLSV (SEQ ID NO: 10) | QRVNLIV (SEQ ID NO: 15) | RSDVLSE (SEQ ID NO: 12) | QRNHRTT (SEQ ID NO: 13) |
| AAACTGCAAAAG (SEQ ID NO: 9) 8196 | RSDNLGV (SEQ ID NO: 16) | QKINLQV (SEQ ID NO: 17) | RSDVLSE (SEQ ID NO: 12) | QRNHRTT (SEQ ID NO: 13) |
| AAACTGCAAAAG (SEQ ID NO: 9) 8196z | RSDNLSV (SEQ ID NO: 10) | QKINLQV (SEQ ID NO: 17) | RSDVLSE (SEQ ID NO: 12) | QRNHRTT (SEQ ID NO: 13) |
| AAACTGCAAAAG (SEQ ID NO: 9) 8196zg | RSDNLGV (SEQ ID NO: 16) | QKINLQV (SEQ ID NO: 17) | RSDVLSE (SEQ ID NO: 12) | QRNHRTT (SEQ ID NO: 13) |

TABLE 1-continued

Zinc finger nucleases targeted to the human CCR-5 gene

| Target sequence | F1 | F2 | F3 | F4 |
|---|---|---|---|---|
| AAACTGCAAAAG (SEQ ID NO: 9) 7568 | RSDHLSE (SEQ ID NO: 18) | QNANRIT (SEQ ID NO: 11) | RSDVLSE (SEQ ID NO: 12) | QRNHRTT (SEQ ID NO: 13) |
| r627 designs | | | | |
| GACAAGCAGCGG (SEQ ID NO: 19) 7524 | RSAHLSE (SEQ ID NO: 20) | RSANLSE (SEQ ID NO: 21) | RSANLSV (SEQ ID NO: 22) | DRANLSR (SEQ ID NO: 23) |
| 633 designs | | | | |
| CATCTGcTACTCG (SEQ ID NO: 24) 8040 | RSDSLSK (SEQ ID NO: 25) | DNSNRIK (SEQ ID NO: 26) | RSAVLSE (SEQ ID NO: 27) | TNSNRIT (SEQ ID NO: 28) |

As described below, in certain embodiments, a four-finger binding domain as shown in Table 1 is fused to a cleavage half-domain, such as, for example, the cleavage domain of a Type IIs restriction endonuclease such as FokI. A pair of such zinc finger/nuclease half-domain fusions are used for targeted cleavage, as disclosed, for example, in U.S. Patent Publication No. 20050064474 (application Ser. No. 10/912,932). For example, ZFN-215 denotes the pair of fusion proteins containing the zinc finger binding domains designated 8267 (which recognizes the target sequence shown in SEQ ID NO:1 and comprises the 4 recognition helices depicted in SEQ ID NOs:2, 6, 4 and 8) and 8196z (which recognizes the target sequence shown in SEQ ID NO:9 and comprises the 4 recognition helices depicted in SEQ ID NOs:10, 17, 12 and 13). ZFN-201 denotes the pair of fusion proteins containing the zinc finger binding domains designated 8266 (which recognizes the target sequence shown in SEQ ID NO:1 and comprises the 4 recognition helices depicted in SEQ ID NOs: 2, 2, 4 and 8) and 8196z (which recognizes the target sequence shown in SEQ ID NO:9 and comprises the 4 recognition helices depicted in SEQ ID NOs:10, 17, 12 and 13).

For targeted cleavage, the near edges of the binding sites can separated by 5 or more nucleotide pairs, and each of the fusion proteins can bind to an opposite strand of the DNA target. Hence, any one of the proteins identified as an "r162 design" in Table 1 (indicating that it binds to the reverse strand and that the downstream edge of its binding site is at nucleotide 162) can be paired with any of the proteins identified as a "168 design" (indicating that it binds to the strand opposite that bound by the r162 designs and that the upstream edge of its binding site is at nucleotide 168). For example, protein 8267 can be paired with protein 8196 or with protein 8196z or with any of the other 168 designs; and protein 8266 can be paired with either of proteins 8196 or 8196z or with any other of the 168 designs. All pairwise combinations of the r162 and 168 designs can be used for targeted cleavage and mutagenesis of a CCR-5 gene. Similarly, the 7524 protein (or any other r627 design) can be used in conjunction with the 8040 protein (or any other 633 design) to obtain targeted cleavage and mutagenesis of a CCR-5 gene.

The CCR5-ZFNs described herein can be targeted to any sequence in the CCR5 genome. For example, CCR5 genomic sequences (including allelic variants such as CCR5-Δ32) are well known in the art and individuals homozygous for the CCR5-Δ32 (see, e.g., Liu et al. (1996) *Cell* 367-377), are resistant to HIV-1 infection.

B. Cleavage Domains

The ZFNs also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 (application Ser. Nos. 10/912,932 and 11/304,981, respectively) and in U.S. provisional patent application No. 60/808,486 (filed May 25, 2006), the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of Fok I and a second cleavage half-domain includes mutations at amino acid residues 486 and 499. See FIGS. 2, 3 and 4.

Thus, in one embodiment, as shown in FIGS. 3 and 4, the mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of U.S. Provisional Application No. 60/808,486 (filed May 25, 2006), the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Patent Publication No. 20050064474 (Ser. No. 10/912,932, Example 5) and U.S. Patent Provisional Application Ser. No. 60/721,054 (Example 38).

C. Additional Methods for Targeted Cleavage in CCR5

Any nuclease having a target site in a CCR5 gene can be used in the methods disclosed herein. For example, homing endonucleases and meganucleases have very long recognition sequences, some of which are likely to be present, on a statistical basis, once in a human-sized genome. Any such nuclease having a unique target site in a CCR5 gene can be used instead of, or in addition to, a zinc finger nuclease, for targeted cleavage in a CCR5 gene.

Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66.

Delivery

The ZFNs described herein may be delivered to a target cell by any suitable means. Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

ZFNs as described herein may also be delivered using vectors containing sequences encoding one or more ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties.

In certain embodiments, the vector is an adenovirus vector. Thus, described herein are adenovirus (Ad) vectors for introducing heterologous sequences (e.g., zinc finger nucleases (ZFNs)) into cells.

Non-limiting examples of Ad vectors that can be used in the present application include recombinant (such as E1-deleted), conditionally replication competent (such as oncolytic) and/or replication competent Ad vectors derived from human or non-human serotypes (e.g., Ad5, Ad11, Ad35, or porcine adenovirus-3); and/or chimeric Ad vectors (such as Ad5/35) or tropism-altered Ad vectors with engineered fiber (e.g., knob or shaft) proteins (such as peptide insertions within the HI loop of the knob protein). Also useful are "gutless" Ad vectors, e.g., an Ad vector in which all adenovirus genes have been removed, to reduce immunogenicity and to increase the size of the DNA payload. This allows, for example, simultaneous delivery of sequences encoding ZFNs and a donor sequence. Such gutless vectors are especially useful when the donor sequences include large transgenes to be integrated via targeted integration.

Replication-deficient recombinant adenoviral vectors (Ad) can be produced at high titer, and they readily infect a number of different cell types. Most adenovirus vectors are engineered such that a transgene replaces the Ad E1a, E1b, and/or E3 genes; subsequently the replication defective vector is propagated in cells that provide one or more of the deleted gene functions in trans. For example, human 293 cells supply E1 function. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-1089 (1998)).

Additional examples of the use of adenovirus vectors for gene transfer in clinical trials include Rosenecker et al., Infection 24:1 5-10 (1996); Welsh et al., Hum. Gene Ther. 2:205-18 (1995); Alvarez et al., Hum. Gene Ther. 5:597-613 (1997); Topf et al., Gene Ther. 5:507-513 (1998).

In certain embodiments, the Ad vector is a chimeric adenovirus vector, containing sequences from two or more different adenovirus genomes. For example, the Ad vector can be an Ad5/35 vector. Ad5/35 is created by replacing one or more of the fiber protein genes (knob, shaft, tail, penton) of Ad5 with the corresponding fiber protein gene from a B group adenovirus such as, for example, Ad35. The Ad5/35 vector and characteristics of this vector are described, for example, in Ni et al. (2005) "Evaluation of biodistribution and safety of adenovirus vectors containing group B fibers after intravenous injection into baboons," Hum Gene Ther 16:664-677; Nilsson et al. (2004) "Functionally distinct subpopulations of cord blood CD34+ cells are transduced by adenoviral vectors with serotype 5 or 35 tropism," Mol Ther 9:377-388; Nilsson et al. (2004) "Development of an adenoviral vector system with adenovirus serotype 35 tropism; efficient transient gene transfer into primary malignant hematopoietic cells," J Gene Med 6:631-641; Schroers et al. (2004) "Gene transfer into human T lymphocytes and natural killer cells by Ad5/F35 chimeric adenoviral vectors," Exp Hematol 32:536-546; Seshidhar et al. (2003) "Development of adenovirus serotype 35 as a gene transfer vector," Virology 311:384-393; Shayakhmetov et al. (2000) "Efficient gene transfer into human CD34(+) cells by a retargeted adenovirus vector," J Virol 74:2567-2583; and Sova et al. (2004), "A tumor-targeted and conditionally replicating oncolytic adenovirus vector expressing TRAIL for treatment of liver metastases," Mol Ther 9:496-509.

As noted above, ZFNs and polynucleotides encoding these ZFNs may be delivered to any target cell. Generally, for inactivating a gene CCR-5, the cell is an immune cell, for example, a lymphocyte (B-cells, T-cells such as T helper ($T_H$) and T cytotoxic cells ($T_C$), null cells such as natural killer (NK) cells); a mononuclear cell (monocytes, marcophages); a granulocytic cell (granulocytes, neutrophils, eosinophils, basophils); a mast cell; and/or a dendritic cell (Langerhans cells, interstitial dendritic cells, interdigitating dendritic cells, circulating dendritic cells). Macrophages, B lymphocytes and dendritic cells are exemplary antigen-presenting cells involved in $T_H$ cell activation. In certain embodiments, the target cell is a $T_H$ cell, characterized by expression of CD4 on the surface. The target cell may also be a hematopoietic stem cell, which may give rise to any immune cell.

Applications

The disclosed methods and compositions can be used to cleave DNA at a region of interest in cellular chromatin (e.g., at a desired or predetermined site in a genome, for example, in a gene, either mutant or wild-type); to replace a genomic sequence (e.g., a region of interest in cellular chromatin, see, also, Example 5 below) with a homologous non-identical sequence (i.e., targeted recombination); to delete a genomic sequence by cleaving DNA at one or more sites in the genome, which cleavage sites are then joined by non-homologous end joining (NHEJ); to screen for cellular factors that facilitate homologous recombination; to replace a wild-type sequence with a mutant sequence; and/or to convert one allele to a different allele. Such methods also allow for generation and/or modification of cells lines (for therapeutic and non-therapeutic uses), treatment of infections (viral or bacterial) in a host (e.g., by blocking expression of viral or bacterial receptors, thereby preventing infection and/or spread in a host organism); to treat genetic diseases.

Thus, the compositions and methods described herein can be used for gene modification, gene correction, and gene disruption. Non-limiting examples of gene modification includes homology directed repair (HDR)-based targeted integration; HDR-based gene correction; HDR-based gene modification; HDR-based gene disruption; NHEJ-based gene disruption and/or combinations of HDR, NHEJ, and/or single strand annealing (SSA). Single-Strand Annealing (SSA) refers to the repair of a double strand break between two repeated sequences that occur in the same orientation by resection of the DSB by 5'-3' exonucleases to expose the 2 complementary regions. The single-strands encoding the 2 direct repeats then anneal to each other, and the annealed intermediate can be processed such that the single-stranded tails (the portion of the single-stranded DNA that is not annealed to any sequence) are be digested away, the gaps filled in by DNA Polymerase, and the DNA ends rejoined. This results in the deletion of sequences located between the direct repeats.

The compositions (e.g., Ad-ZFN vectors) and methods described herein can also be used in the treatment of various genetic diseases and/or infectious diseases.

The compositions and methods can also be applied to stem cell based therapies, including but not limited to:

(a) Correction of somatic cell mutations by short patch gene conversion or targeted integration for monogenic gene therapy (b) Disruption of dominant negative alleles (c) Disruption of genes required for the entry or productive infection of pathogens into cells (d) Enhanced tissue engineering, for example, by:
(i) Modifying gene activity to promote the differentiation or formation of functional tissues; and/or
(ii) Disrupting gene activity to promote the differentiation or formation of functional tissues (e) Blocking or inducing differentiation, for example, by:
(i) Disrupting genes that block differentiation to promote stem cells to differentiate down a specific lineage pathway
(ii) Targeted insertion of a gene or siRNA expression cassette that can stimulate stem cell differentiation.
(iii) Targeted insertion of a gene or siRNA expression cassette that can block stem cell differentiation and allow better expansion and maintenance of pluripotency (iv) Targeted insertion of a reporter gene in frame with an endogenous gene that is a marker of pluripotency or differentiation state that would allow an easy marker to score differentiation state of stem cells and how changes in media, cytokines, growth conditions, expression of genes, expression of siRNA molecules, exposure to antibodies to cell surface markers, or drugs alter this state.

(f) Somatic cell nuclear transfer, for example, a patient's own somatic cells can be isolated, the intended target gene modified in the appropriate manner, cell clones generated (and quality controlled to ensure genome safety), and the nuclei from these cells isolated and transferred into unfertilized eggs to generate patient-specific hES cells that could be directly injected or differentiated before engrafting into the patient, thereby reducing or eliminating tissue rejection.

(g) Universal stem cells by knocking out MHC receptors— This approach would be used to generate cells of diminished or altogether abolished immunological identity. Cell types for this procedure include but are not limited to, T-cells, B cells, hematopoietic stem cells, and embryonic stem cells. Therefore, these stem cells or their derivatives (differentiated cell types or tissues) could be potentially engrafted into any person regardless of their origin or histocompatibility.

The compositions and methods can also be used for somatic cell therapy (e.g., autologous cell therapy and/or universal T-cell by knocking out MHC receptors, see section (g) above), thereby allowing production of stocks of T-cells that have been modified to enhance their biological properties. Such cells can be infused into a variety of patients independent of the donor source of the T-cells and their histocompatibility to the recipient.

In addition, the use of Ad vectors as described herein to deliver ZFNs enhances rates of NHEJ. Without being bound by one theory, it appears that this effect is due to the inhibitory effect the E4 proteins (E4 ORF6 (E4 34k), E4 ORF3) may have on DSB repair.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting.

EXAMPLES

Example 1

Vector Construction

A. Construction of Ad5/35-GFP and Ad5/35-ZFN Vectors

Chimeric Ad5/35 vectors (Nilsson et al. (2004) Mol Ther 9:377-388; Nilsson et al. (2004) J Gene Med 6:631-641) were constructed as shown schematically in FIG. 1. Briefly, a sequence encoding an expression cassette for GFP (top line), an expression cassette for a pair of engineered ZFNs (ZFN1 and ZFN2) which target the endogenous CCR5 locus (middle line), or a homologous donor sequence for targeting a 47-bp patch sequence in the CCR5 locus (bottom line) was inserted in place of the E1 genes using the AdEasy bacterial recombination system (Stratagene).

The Ad-215 and Ad-201 vector constructs each comprise sequences encoding two ZFNs that cleave the endogenous CCR5 gene at sequences encoding Leu55. Both ZFNs are expressed under the control of a single promoter via a 2A fusion. As shown in Table 1 above, the ZFN215 pair encoded by the Ad-215 construct comprise zinc finger binding domains 8267 and 8196z from the r162 and 168 designs, respectively; while the ZFN201 pair encoded by the Ad-201 vector comprises zinc finger binding domains 8266 and 8196z from the r162 and 168 designs, respectively. The ZFNs encoded by the Ad-215 and Ad-201 vectors are fused to a wild-type FokI cleavage half-domain. See FIG. 2.

The ZFN224 pair encoded by the Ad-224 construct comprise zinc finger binding domains 8267 and 8196z from the r162 and 168 designs, respectively. Thus, The Ad-224 construct has the same zinc finger proteins as Ad-215. However, the ZFNs encoded by the Ad-224 construct contain mutant FokI cleavage-half domain as described in U.S. Provisional Application No. 60/808,486 (filed May 25, 2006), and incorporated herein by reference in its entirety. In particular, the 8267 zinc finger domain is fused to a FokI cleavage half-domain containing the Q486E and I499L mutations (FIG. 3), and 8196z zinc finger domain is fused to a FokI cleavage half-domain containing the E490K and I538K mutations (FIG. 4).

B. Donor Vector for Targeted Insertion

To make a donor vector (Ad5/35 P ori, FIG. 1 bottom line), an 1881-bp fragment of the human genome corresponding to the CCR5 locus was PCR amplified and cloned into the PCR4-TOPO vector (Invitrogen). The sequence of the fragment is shown in FIG. 5 (SEQ ID NO:36).

In order to generate a cloning site at which to insert a "patch" sequence, 2 nucleotides of the sequence shown in FIG. 5 were changed to generate a XbaI recognition site. Specifically, the nucleotide sequence "atcctgataa" (SEQ ID NO:39) (nucleotides 470-479 in the donor fragment) was changed to "atctagataa" (SEQ ID NO:40) (the 2 bases changed are underlined) via the QuickChange Site-Directed Mutagenesis Kit (Stratagene).

The resulting DNA sequence was then digested with XbaI, and a 47 bp "patch" sequence, shown in FIG. 6 (SEQ ID NO:37), was inserted at the XbaI site.

The resulting sequence, shown in FIG. 7 (SEQ ID NO:38), was inserted into the Ad5/35 vector as described above for the GFP and ZFN expression cassettes. With respect to the sequence shown in FIG. 7, the 5'homology arm correspond to nucleotides 1-471; the "patch" sequence for targeted insertion into CCR-5 is underlined and corresponds to nucleotides 472-518; and the 3' homology arm corresponds to nucleotides 519-1928.

Example 2

Transduction of hES Cells with Ad5/35-GFP Vectors

Chimeric Ad5/35-GFP vectors as described in Example 1 were introduced into human embryonic stem (hES) cells as follows.

Infections of hES cells were performed in 500 µl volumes using 400,000 cells and 25 µl, 5 µl or 0.5 µl of the Ad5/35-GFP vector (MOI of 8200, 1640 and 164 respectively). After 4 hours, the cells were washed and plated onto fresh murine embryonic fibroblast (MEF) feeder cells. Fluorescence microscopy of living cells, obtained approximately 20 hours post-infection, showed fluorescence in stem cell colonies that had been infected with 5 and 25 µl of virus, and no fluorescence in the feeder cells. FACS analysis for GFP fluorescence was performed ~22 hours post-infection. The results are shown in Table 2.

TABLE 2

| Infection | % of fluorescent T-cells |
|---|---|
| Mock infection | 0.74% |
| Ad5/35-GFP 0.5 µl | 39.4% |
| Ad5/35-GFP 5 µl | 91% |
| Ad5/35-GFP 25 µl | 95% |

These results indicate that Ad5/35 vectors are capable of infecting human embryonic stem cells at high efficiency.

Example 3

Modification of the CCR-5 Gene Using Ad5/35-ZFNs

CD4$^+$ T-cells and PBMCs were obtained from AllCells. Cells were cultured in RPMI+10% FBS+1% L-Glutamine (30 mg/mL)+IL-2 (1 ng/mL, Sigma) and activated with anti CD3-CD28 beads according to manufacturer's protocol (Dynal). Cells were seeded at 3E5 cell/mL in 1 mL volume in a 24 well plate.

Adenoviral vectors as described in Example 1 (Ad5/35 GFP, Ad5/35 215 or Ad5/35 224) were added two days later at an MOI of 10, 30, or 100 (MOI calculated based on infectious titer).

Cells were harvested 2 days after exposure to virus and gene modification efficiency was determined using a Cel-1 assay, performed as described in International Patent Publication WO 07/014,275. See, also, Oleykowski et al. (1998) *Nucleic Acids res.* 26:4597-4602; Qui et al. (2004) *BioTechniques* 36:702-707; Yeung et al. (2005) *BioTechniques* 38:749-758.

Results are shown in Table 3.

TABLE 3

| | % CCR-5 Alleles Modified | |
|---|---|---|
| | PBMCs | CD4+ T-cells |
| Control | not detectable | not detectable |
| Ad5/35-ZFN215 at MOI 10 | 6.1 | 6.7 |
| Ad5/35-ZFN215 at MOI 30 | 14.0 | 16.5 |
| Ad5/35-ZFN215 at MOI 100 | 31.2 | 32.3 |
| Ad5/35-ZFN224 at MOI 10 | 3.6 | 1.8 |
| Ad5/35-ZFN224 at MOI 30 | 7.4 | 9.0 |
| Ad5/35-ZFN224 at MOI 100 | 15.0 | 14.9 |
| Ad5/35-GFP at MOI 10 | not detectable | not detectable |
| Ad5/35-GFP at MOI 30 | not detectable | not detectable |

These results indicate that gene modification was observed after infection of cells with Ad5/35 vectors encoding both the ZFN215 nuclease pair (comprising wild type FokI cleavage half-domains) and the ZFN 224 nuclease pair (comprising the mutant FokI cleavage half-domains described in Example 1A). In addition, the results show that gene modification levels increased in a dose-dependent manner.

To determine the persistence of ZFN-induced gene modification, infected cells were kept in culture for another 8 days (same culture medium as before). Cells were counted and diluted with fresh medium every 2 days. Cells were then harvested (10 days after viral transduction) and the Cel-1 assay was repeated. In addition, a fraction of the CD4$^+$ T-cell population was re-activated with anti CD3/CD28 beads (Dynal) on day 7. Results are shown in Table 4.

TABLE 4

| | % Cells Infected | |
|---|---|---|
| | Re-activated CD4 | Non-activated CD4 |
| Control | not detectable | not detectable |
| Ad5/35-ZFN215 at MOI 30 | 10.1 | 10.9 |
| Ad5/35-ZFN215 at MOI 100 | 29.0 | 28.2 |
| Ad5/35-ZFN224 at MOI 30 | 6.7 | 6.4 |
| Ad5/35-ZFN224 at MOI 100 | 16.1 | 16.6 |
| Ad5/35-GFP at MOI 100 | not detectable | not detectable |

These results show that the degree of gene modification was maintained as the CD4$^+$ T-cells expanded. Furthermore, reactivation had no apparent effect on the growth of the modified cells as compared to unmodified cells.

Example 4

Modification of the CCR-5 Gene Using Ad5/35-ZFNs in CD34+ Cells

CD4$^+$ T-cells and CD34$^+$ cells were obtained from All-Cells. On day 0, CD4$^+$ T-cells were cultured in RPMI+10% FBS+1% L-Glutamine (30 mg/mL)+IL-2 (1 ng/mL, Sigma) and activated with anti CD3-CD28 beads according to the manufacturer's protocol (Dynal). CD34$^+$ cells were cultured in serum free medium (Stemspan H3000, Stem Cell Technologies) and supplemented with cytokines (Stemspan CC100, Stem Cell Technologies). Cells were seeded at 6E5 cell/mL in 1 mL volume in 24 well plates. Adenoviral vectors (Ad5/35 GFP or Ad5/35 224) were added the next day (day 1) at different MOIs (MOI calculated based on infectious titer).

Cells were harvested on day 4 and gene modification efficiencies were determined using a Cel-1 assay.

For CD4$^+$ T-cells, Ad5/35 224 induced CCR-5 gene modification with an efficiency of 18.0%, 34.5% and 48.4% at MOIs of 25, 50 and 100, respectively.

Similarly, for CD34$^+$ cells, Ad5/35 224 induced CCR5 gene modification at efficiencies of 10.9% and 11.1%, at MOIs of 10 and 50, respectively.

Example 5

Targeted Insertion of an Exogenous Sequence into the CCR-5 Gene Using Ad5/35-ZFNs On day 0, CD4$^+$ T-cells were cultured in RPMI+10% FBS+ 1% L-Glutamine (30 mg/mL)+IL-2 (1 ng/mL, Sigma) and activated with anti CD3-CD28 beads according to the manufacturer's protocol (Dynal). Cells were seeded at 3E5 cells/mL in 1 mL volume in a 24 well plate. Two days later (day 2), cells were co-transduced with different combinations of Ad5/35 224 and Ad5/35 P on donor (FIGS. 1 and 7). Ad5/35 224 was added at MOIs of 0, 25, 50, and 100, and Ad5/35 P ori donor was added at MOIs of 0, 100, and 300 (MOI calculated based on infectious titer). Cells were harvested 2 days after infection (day 4) and the targeted integration efficiency was determined by RFLP assay, as follows.

Genomic DNA was isolated from transduced cells and PCR amplified with primers outside the region of donor homology. The amplified fragment was then incubated with the restriction enzyme BglI, whose recognition site is contained within the P ori donor (Patch) sequence. The frequency of targeted integration of the Patch sequence was calculated by determining the ratio of cleaved to un-cleaved products.

The frequency of targeted integration of the Patch sequence was 3.1% when cells were co-transduced with Ad5/35 224 at an MOI of 50 and Ad5/35 P ori at an MOI of 300.

Example 6

Non-Homologous End Joining Induced Using Ad5/35-ZFPs

To determine the types of ZFN-mediated mutations generated by targeted cleavage followed by non-homologous end joining (NHEJ), genomic CCR-5 sequence of modified cells were sequenced and analyzed. Briefly, PBMCs and CD4+ T-cells, transduced with Ad5/35 ZFN 215 in the same manner as described in Example 3, were harvested and genomic DNA was extracted from these cells. The CCR5 locus was then PCR amplified, Topo cloned into the PCR4-TOPO vector (Invitrogen), and bacterial clones were sequence analyzed and compared to the wild-type CCR5 locus.

Mutations induced by targeted ZFN cleavage included both deletions and insertions, and the size of such changes varied over a wide range. Both deletions and insertions as short as a single nucleotide pair were observed, as were insertions of up to almost 100 nucleotide pairs. The sequences of some exemplary mutations induced by targeted, ZFN-mediated cleavage are shown in FIGS. 8-10.

FIG. 8 shows the sequences of a number of deletions identified during the analysis. Missing base pairs are denoted with periods.

An insertion of 5 base pairs occurred at a high frequency in ZFN-treated cells. This 5 base-pair insertion is a duplication of the 5 base-pair sequence between the ZFN-binding sites, converting the sequence GTCATCCTCATCCT-GATAAACTGCAAAAG (SEQ ID NO:41) to GTCATCCT-CATCCTGATCTGATAAACTGCAAAAG (SEQ ID NO:42), with the inserted sequence underlined.

Another frequently-observed mutation was a four base-pair insertion between the two ZFN binding sites, converting the sequence GTCATCCTCATCCTGATAAACTG-CAAAAG (SEQ ID NO:41) to GTCATCCTCATCCT TCTAGATAAACTGCAAAAG (SEQ ID NO:45), with the inserted sequence underlined.

FIG. 9 shows the nucleotide sequences of additional mutations. In one case, a combination of a one-nucleotide deletion and a five-nucleotide insertion was observed.

FIG. 10 shows the sequences of a number of longer insertions resulting from targeted ZFN cleavage.

A summary of the sequence modifications to the CCR-5 locus is shown below in Table 5.

TABLE 5

| TYPE OF MUTATION | | NUMBER IN EACH CELL TYPE | | |
|---|---|---|---|---|
| | | PBMCs | CD4+ T-cells | TOTALS |
| Deletion | | 10 | 8 | 18 |
| Insertions | 5 bp | 11 | 14 | 25 |
| | 4 bp | 8 | 2 | 10 |
| | Other | 3 | 3 | 6 |
| | long | 1 | 3 | 4 |
| Wild-type | | 10 | 14 | 24 |
| Totals | | 43 | 44 | 87 |

Example 7

Cell Viability Post Ad5/35-ZFN Transduction

Cell viability post-transduction with Ad5/35-ZFN constructs was also assessed. Briefly, CD4+ T-cells and PBMCs were obtained from AllCells. On day 0, cells were cultured in RPMI+10% FBS+1% L-Glutamine (30 mg/mL)+IL-2 (1 ng/mL, Sigma) and activated with anti CD3-CD28 beads according to the manufacturer's protocol (Dynal). Cells were seeded at 3E5 cell/mL in 1 mL volume in 24 well plates. Adenoviral vectors (Ad5/35 GFP, Ad5/35 215 or Ad5/35 224) were added two days later (day 2) at MOI of 10, 30, and 100 (MOI calculated based on infectious titer). Cell counts and cell viability were measured at days 4, 6, 8, 10 and 12 using the VIACOUNT protocol provided with the GUAVA analytic flow cytometer, following the manufacturer's instructions (Guava Technologies).

Ad5/35 ZFNs were generally well tolerated, with at least 75% of the cells (up to 90% at the lower MOI) being viable at all time points. Thus, minimal toxicity was observed.

Example 8

Cell Growth Post Ad5/35-ZFN Transduction

Cell growth (doubling) post-transduction with Ad5/35-ZFN constructs was also assessed.

On day 0, CD4+ T-cells and PBMCs were cultured in RPMI+10% FBS+1% L-Glutamine (30 mg/mL)+IL-2 (1 ng/mL, Sigma). Cells were activated on days 0 and 6 with anti CD3-CD28 beads according to the manufacturer's protocol (Dynal). Cells were initially seeded at 3E5 cell/mL in 1 mL volume in 24 well plates. Adenoviral vectors (Ad5/35 GFP, Ad5/35 215 or Ad5/35 224) were added on day 2 at MOIs of 10, 30, or 100 (MOI calculated based on infectious titer). Cell counts and cell viability were measured using the VIACOUNT protocol provided with the GUAVA analytic flow cytometer as described in Example 7.

Cell growth or doubling was minimally affected by the adenovirus (except for Ad5/35 215 at a MOI of 100). Overall, at least 8 doublings (i.e., >100-fold expansion) were achieved over a 14 day period in both CD4+ T-cells and PBMCs.

Example 9

Measuring Persistence of Adenovirus Genome in CD4+ T-Cells

CD4+ T-cells were cultured in RPMI+10% FBS+1% L-Glutamine (30 mg/mL)+IL-2 (1 ng/mL, Sigma) and activated with anti CD3-CD28 beads according to the manufacturer's protocol (Dynal). Cells were seeded at 6E5 cell/mL in 1 mL volume in a 24 well plate. Adenoviral vectors (Ad5/35 215 or Ad5/35 224) were added the next day at MOI of 10, 30 and 100 (MOI calculated based on infectious titer). Cells were harvested on days 4 and 14. DNA was extracted with a Masterpure kit (Epicenter Biotechnologies). Persistence of adenoviral genomes was quantified by presence of Ad genomic DNA as measured by TaqMan® PCR (Applied Biosystem). Primer/probes were designed to target and detect the E4 region of the adenoviral genome. Detection limit of the TaqMan® PCR protocol is ~$10^{-4}$ adenoviral genome per cell.

Overall, between 2 days and 12 days post-transduction, the level of adenoviral genomes per cell decreased by 100-1000 fold. Less than $10^{-2}$ genome per cell was detected at the highest MOI (100) by day 12 post transduction.

Example 10

Measuring Persistence of Protein Expression in CD4+ T-Cells

On day 0, CD4+ T-cells were cultured and activated as described in Example 9. Adenoviral vectors (Ad5/35 GFP)

were added the day after activation (day 1) at MOIs of 50, 100, 250 and 500 (MOI calculated based on infectious titer). Percent GFP-positive cells and mean fluorescent intensity (MFI) was determined by GUAVA analytical flow cytometry every 2-3 days.

Significant GFP expression was observed initially (day 3) at all MOIs. GFP fluorescence persisted through day 13, from 80-100% of cells GFP positive on day 3 to 30-60% of cells GFP positive on day 13. However, MFI decreased significantly over the same period (by almost 100 fold), suggesting that even though cells on day 13 were scored as GFP positive by the flow cytometer, they contained significantly less GFP protein. In addition, it is well known that GFP has a relatively long half-life (>24 hrs).

Example 11

Measuring ZFN mRNA in CD4+ T-Cells Transduced with Ad5/35-ZFN Vectors

On day 0, CD4+ T-cells were cultured and activated as described in Example 9. Adenoviral vectors (Ad5/35 215 or Ad5/35 224) were added the next day (day 1) at MOIs of 30 and 100 (MOI calculated based on infectious titer). Cells were harvested on days 3 and 9 (i.e., 2 and 8 days post-transduction), and RNA was extracted with a High Pure® RNA isolation kit (Roche). ZFN mRNA was quantified by RT-TaqMan® PCR (Applied Biosystems). The primer/probe set was designed and optimized to anneal to sequences encoding the Fok I cleavage half-domain.

Significant amounts of ZFN mRNA were detected ($1 \times 10^5$-$1 \times 10^6$ copies per cell depending on MOI) 2 days post-transduction. However, by 8 days post-transduction, ZFN mRNA levels in all but one sample (Ad5/35 215 at MOI of 100) were below the detection limit of the assay. Approximately 100 copies/cell were detected in the Ad5/35 215 MOI 100 sample; representing a thousand-fold decrease in mRNA levels between 2 and 8 days post-transduction.

Example 12

Disruption of the CCR-5 Gene in Primary Human CD4+ T-Cells Using Ad5/35-ZFN Vectors Primary human CD4+ T-cells (obtained from donors at Univ. of Pennsylvania) were mock transduced or transduced with either the Ad5/35 GFP, Ad5/35 215 or Ad5/35 224.

On day 1, the T-cells were pelleted and resuspended to a concentration of $1 \times 10^6$/ml in Xvivo 15 (BioWhittaker, Walkersville, Md.) supplemented with 10% fetal calf serum and 1% L-Glutamine. One ml of cells was exposed to anti-CD3/CD28 beads (prepared as described by Levine et al. (1997) *J. Immunol.* 159:5921-5930). The next day (day 2) $1 \times 10^6$ cells were transduced with the Ad5/35 GFP, Ad5/35 215 or Ad5/35 224 vectors at an MOI of 30 or 100. The following day the volume of medium was doubled with Xvivo15 containing 10% fetal calf serum, 1% L-Glutamine, 0.9% N-acetylcysteine, and 300 IU/ml human recombinant IL-2. For each condition, cells were counted every 2 days on a Coulter Counter, a test sample was pelleted for analysis, and the remaining culture was seeded and fed to $1 \times 10^6$ cells/ml. On day 6, beads were removed using a magnet, and the cells were cultured with the Xvivo15/FCS/L-Glut/NAC/IL2 medium described above. On-day 8, a fraction of cells from each sample was pelleted for analysis by Cel-1 and the remaining cells in each sample (at a concentration of $1 \times 10^6$ cells/ml) were infected with the CCR5 tropic HIV-1 strain US1 at an MOI of 0.1 (see Example 13).

Every two days cells were counted, pelleted, a small amount was collected for analysis by Cel-1, and the remaining cells were seeded and fed with the same Xvivo15/FCS/L-glut/NAC/IL2 containing medium.

On Day 13, re-stimulation of CD4+ T-cell cultures was performed with a mix of irradiated (3000 rad) allogeneic PBMCs and irradiated (10,000 rad) K562 cells expressing CD32 plus OKT3 (anti-CD3) and anti-CD28.

Genomic DNA was harvested 13 days post-transduction and the CCR5 disruption efficiency was measured by the Cel-1 assay. Results are shown in Table 6.

TABLE 6

|  | GFP | | Ad/ZFN 215 | | Ad/ZFN 224 | |
| --- | --- | --- | --- | --- | --- | --- |
| MOI Control | 30 | 100 | 30 | 100 | 30 | 100 |
| Percentage of alleles modified  0 | 0 | 0 | 54 | 44 | 44 | 30 |

Example 13

HIV Challenge

In addition, the primary human CD4+ T-cells transduced with Ad5/35 vectors as described in Example 12 were diluted 1:3 with untransduced cells and either mock-infected or infected (MOI of 0.1) with a replication competent HIV strain, US1. These cells were then passaged to allow multiple rounds of HIV infection and replication. A small amount of cells were isolated on each of days 0, 5, 11, and 17 post-infection from both the mock- and HIV-infected cultures to monitor the percentage of cells containing disrupted CCR5 genes. Genomic DNA was isolated from each cell sample and the presence of mutant CCR5 alleles was determined using a Cel-1 assay.

Figure 11:
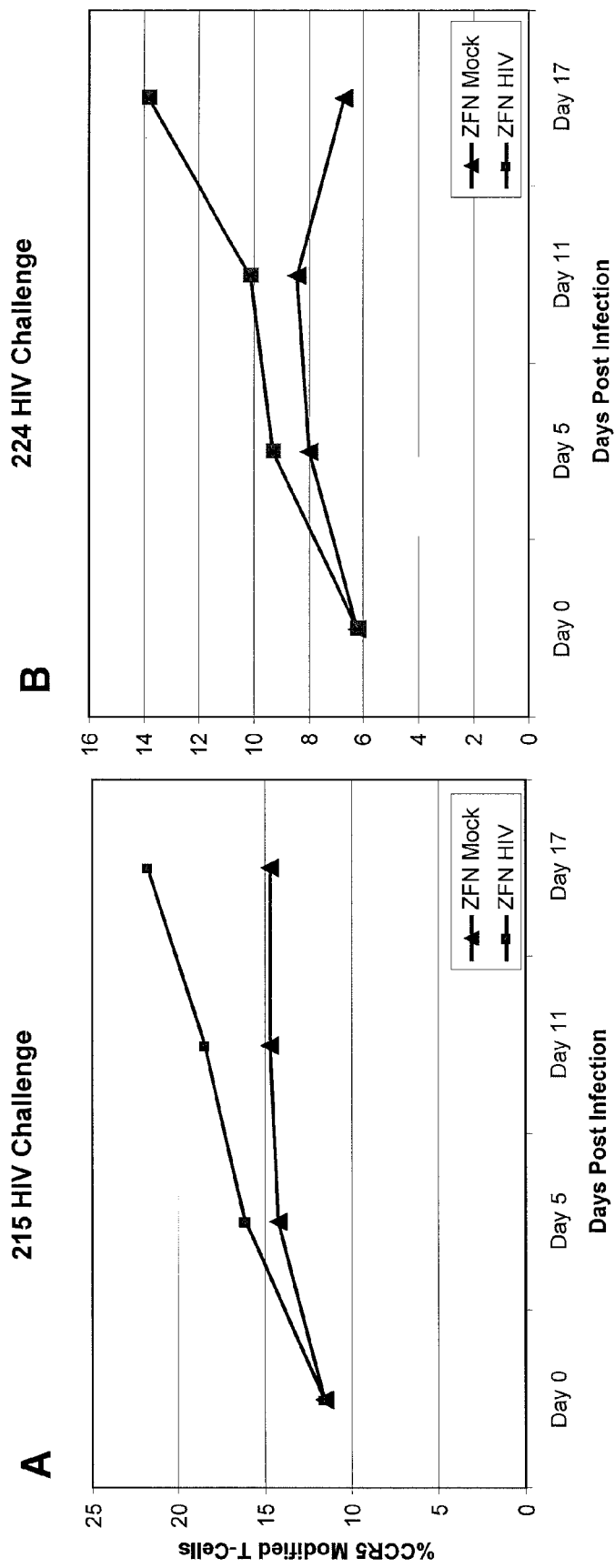
FIG. 11, panels A and B, depict the time course of percentage of CCR-5 modified T-cells in T-cells transduced with Ad5/35 ZFN215 (Panel A) and Ad5/35 ZFN 224 (Panel B), following challenge with wild-type HIV or mock infection.

Results are shown in FIG. 11 panels A (Ad5/35 215 transduced cells) and B (Ad5/35 224 transduced cells) and indicate that, in cells that had been transfected with Ad ZFN vectors, the number of cells containing sequence alterations in their CCR-5 gene increased after HIV infection (ZFN HIV) but did not increase in cells that had not been infected with HIV (ZFN mock).

Example 14

ZFN Disruption of CCR5 in GHOST-CCR5 Cells

A. Determination of ZFN-Induced Mutations in GHOST-CCR5 Cells

Figure 12:
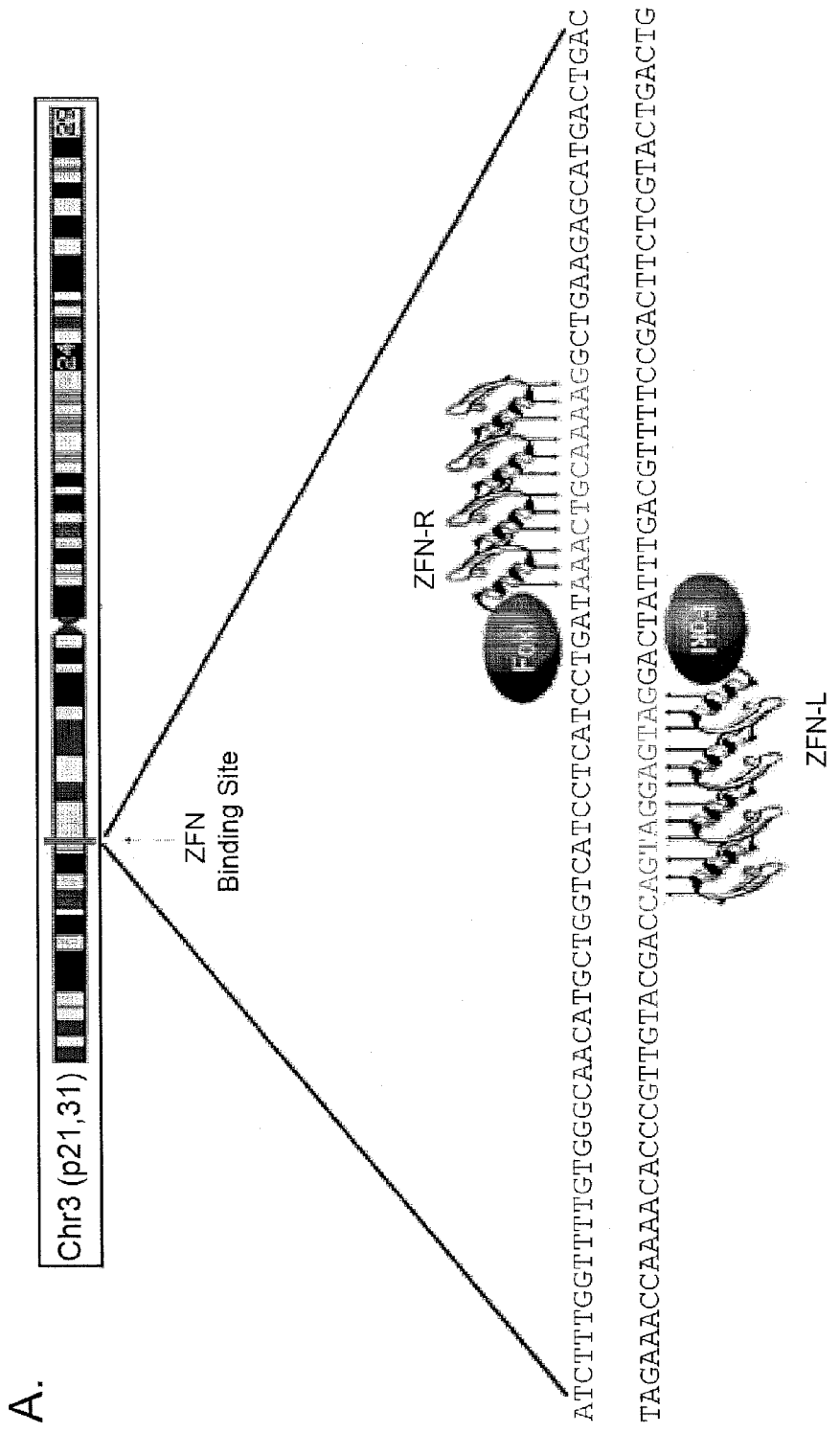
FIG. 12 (SEQ ID NOS: 67 and 68) is a schematic depicting the target sites in the CCR5 gene for CCR5-ZFNs pairs 215 and 224.

GHOST-CCR5 cells, a reporter cell line for HIV-1 infection containing multiple (~4) copies of an autologous CCR5 expression cassette and an inducible GFP marker gene under the control of the HIV-2 LTR (Morner et al. (1999) *J. Virol.* 73:2343-2349), were obtained from the NIH AIDS Research and Reference Reagent Program and transduced with an Adenovirus (Ad5/35) vector (Schroers et al. (2004) *Experimental Hematology* 32:536-546) encoding the CCR5-ZFN pairs 215 (see above text related to Table 1) and 224 (containing the ZFNs denoted in Table 1 as 8196z and 8266). Binding sites for both of these of the ZFN pairs are the same and are shown in FIG. 12.

Induction of ZFN-mediated mutations at the target site was determined using an assay based upon the Surveyor™ nuclease (Transgenomic), also known as Cel-1, a mismatch sensitive enzyme that cleaves DNA at the site of ZFN-induced mutations. Briefly, genomic DNA was extracted from modified and control cells using the MasturePure™ DNA purification kit (Epicentre Biotechnologies) and supplemented with 5 uCi α-$P^{32}$ dATP and 5 uCi α-$P^{32}$ dCTP for radioactive PCR.

Radioactive PCR (50 μl reactions) was performed (AccuPrime™ PCR kit (Invitrogen)) on 100 ng of the genomic DNA extracted from modified and control cells. Briefly, a 292-bp fragment of the CCR5 locus encompassing the CCR5-ZFN target site was amplified for 30 cycles (95° C.—30 sec., 60° C.—30 sec., and 68° C.—30 sec.) using the primers C5_Cel_160_F1: AAGATGGATTATCAAGTGT-CAAGTCC (SEQ ID NO:29); and C5_Cel_160R1: CAAAGTCCCACTGGGCG (SEQ ID NO:30).

The PCR product was spun through a G-50 column (GE Healthcare) and 1 μl of the purified product was mixed with 1 μl of 10× annealing buffer (1× annealing buffer—10 mM Tris, 100 mM NaCl) and water to a final volume of 10 μl. The DNA was denatured and re-annealed in a PCR block using a program that allows heteroduplexes to form (95° C.—10 min; 95° C. to 85° C. at −2° C./s; and 85° C. to 25° C. at −0.1° C./s). After re-annealing, 10 of the Surveyor™ nuclease (Transgenomics), 1 μl 10× AccuPrime™ PCR buffer II, and water were added to a total volume of 20 μl. The reaction was incubated at 42° C. for 20 min to digest heteroduplexes, and the cleaved products were resolved on a non-denaturing 10% TBE polyacrylamide gel (Bio-Rad). The gel was dried and analyzed using a Phosphorimager®. The level of ZFN-induced target gene disruption was determined by obtaining the ratio of the uncleaved parental fragment to the two faster-migrating cleaved products. The proportion of ZFN-disrupted CCR5 alleles in the original sample was calculated using the formula: $(1-\sqrt{(\text{Parental fraction})}) \times 100$. The assay is sensitive to single nucleotide changes and has a detection limit of ~1% ZFN-modified alleles.

Figure 13:
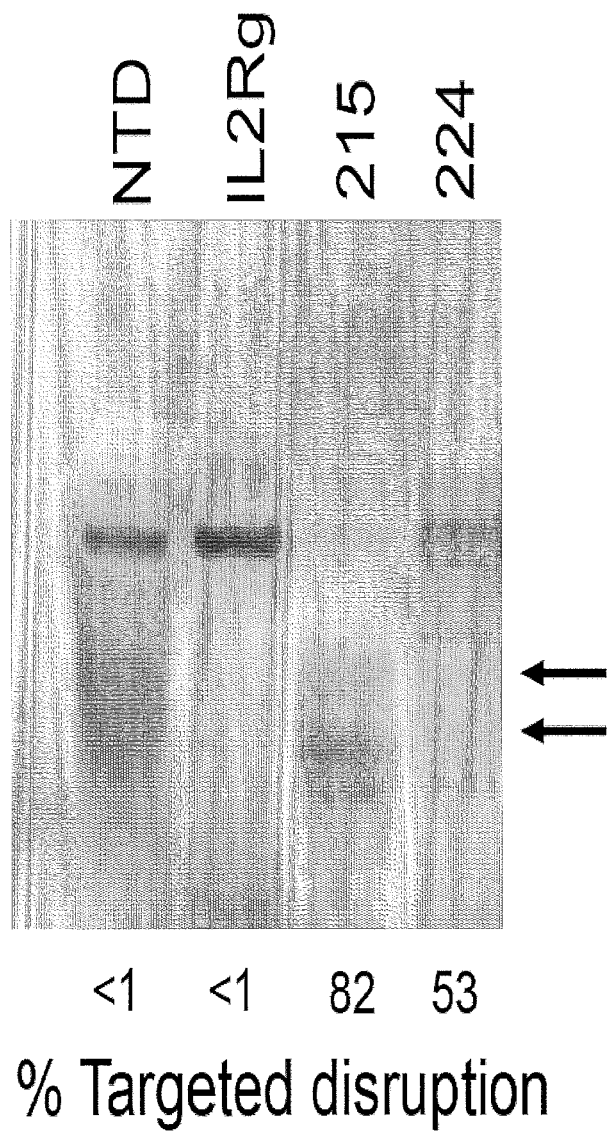
FIG. 13 shows levels of target gene disruption in GHOST-CCR5 cells transduced with an Ad5/35 vector encoding the indicated ZFNs targeting either CCR5 or IL2-Rγ. See Example 14. Lower migrating products (indicated by arrows) are a direct measure of ZFN-mediated gene disruption. "NTD" indicates non-transduced cells.

The results, shown in FIG. 13, demonstrated that CCR5-ZFNs as described herein are highly efficient (50-80%) in mutating CCR5 in GHOST-CCR5 cells (lanes 3 and 4). Non-transduced control cells (lane 1) and cells transduced with an Ad5/35 vector encoding IL-2Rγ-specific ZFNs (Urnov et al. (2005) *Nature* 435:646-651; lane 2) did not exhibit any detectable CCR5 modification, indicating the results were CCR-5-ZFN specific.

B. HIV Challenge

In addition, the transduced cell populations were maintained in culture and one week later were infected with HIV-$1_{BAL}$, a prototype CCR5-tropic HIV-1 isolate. Challenge viruses were obtained from the NIH AIDS Research and Reference Reagent Program and propagated in CD8-depleted PBMC to generate working stocks.

Figure 14A:
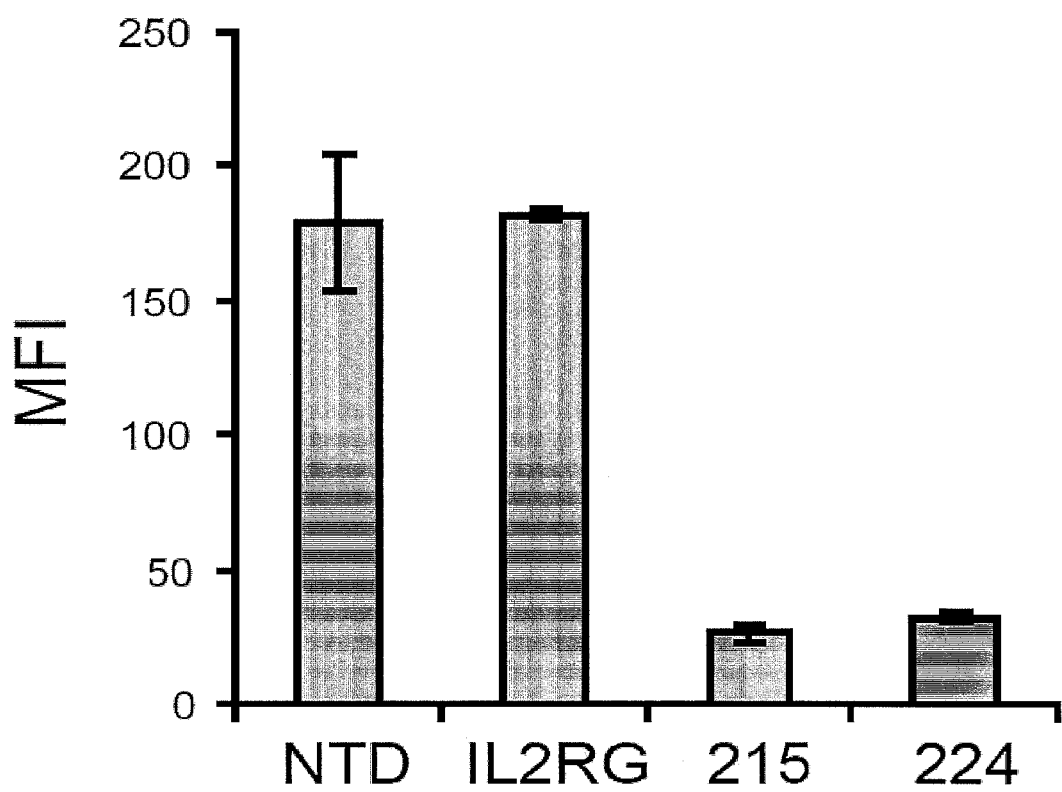
FIG. 14A depicts decreased CCR5 surface expression as measured by flow cytometry in GHOST-CCR5 cells transduced with the indicated vector. NTD refers to non-transduced; IL2R refers to cells containing IL2Rγ-targeted ZFNs; 215 and 224 refer to cells containing ZFN pair 215 or 224, respectively. "MFI" indicates mean fluorescence intensity.

Immediately prior to HIV-1 infection, CCR5 surface expression was analyzed and shown to be reduced by >10-fold in the pools of CCR5-ZFN transduced cells compared to control cells treated with IL2Rγ-ZFNs (FIG. 14A).

Figure 14B:
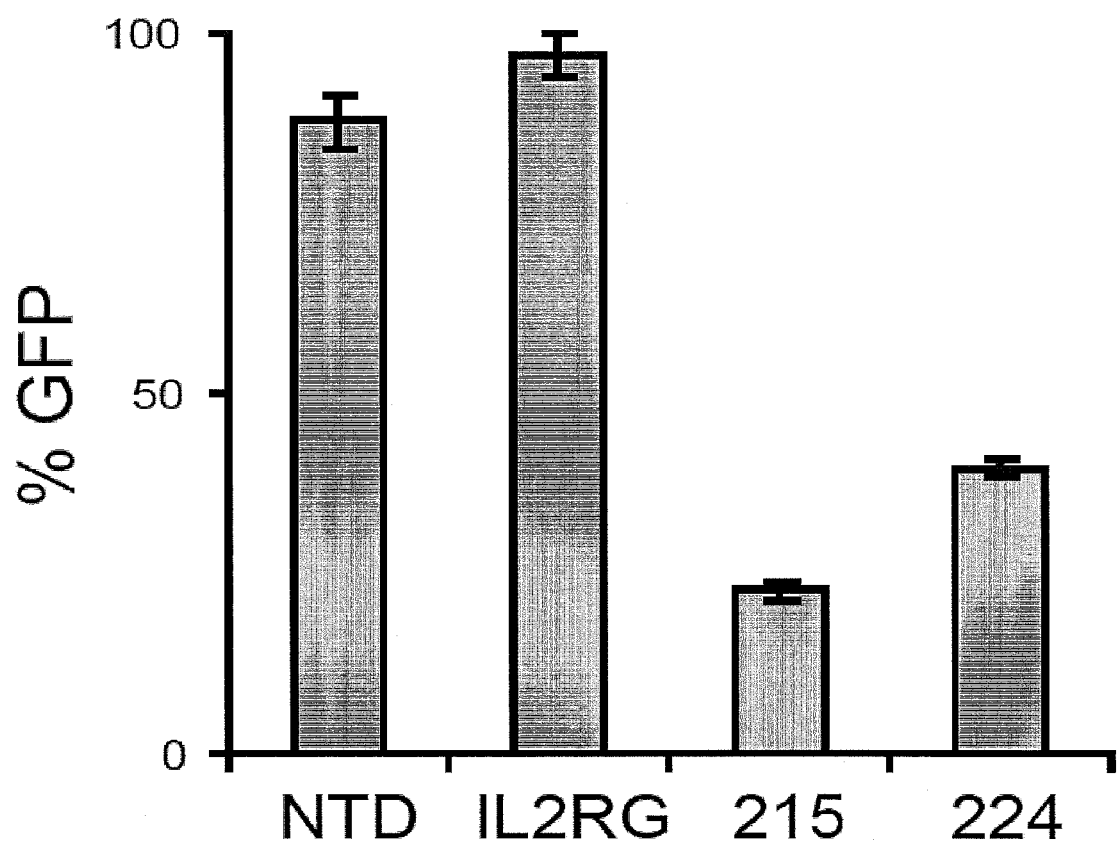
FIG. 14B shows protection from challenge with HIV-1$_{BAL}$ as measured by flow cytometry 48 hours after HIV challenge of CCR5-ZFN215 and CCCR-ZFN224 modified cells compared to IL-2rγ ZFN and control GHOST-CCR cells. GFP fluorescence indicates HIV entry and is plotted as an average percent infected relative to positive control. Bar graphs represent averages of triplicates.

Results of the HIV-$1_{BAL}$ challenge demonstrated a substantial decrease in HIV-1 infection in CCR5-ZFN treated samples after one week, as measured by loss of HIV LTR-driven GFP induction 48 hours after infection (FIG. 14B). Genetic modification at the intended target site within CCR5 was confirmed through sequencing of genomic DNA from the CCR5-ZFN treated GHOST-CCR5 cells.

In addition, single cell derived clones isolated from the CCR5-ZFN-transduced GHOST-CCR5 cells were expanded over a period of several weeks. The CCR5 transgene was genotyped and a clone possessing only disrupted CCR5 alleles was tested and shown to be resistant to HIV infection by HIV-1BAL. Introduction of a CCR-5 transgene into these cells restored infectability by HIV, demonstrating that resistance to HIV-1 infection was mediated exclusively by a defect in viral entry via ZFN-mediated CCR5 disruption.

These results show that the CCR5-ZFNs efficiently cleave their DNA target site in the CCR5 gene, and confirm that a high proportion of ZFN-induced mutations prevent CCR5 cell-surface expression, resulting in complete resistance to CCR5-tropic HIV-1 infection.

Example 15

CCR5-ZFN Modification Confers a Survival Advantage

The following experiments were conducted to evaluate if ZFN-mediated disruption of CCR5 would confer the long-term resistance to HIV-1 expected from a permanent genetic change.

A. CCR-5 Disruption after Long-Term Culture

PM1 cells, a $CD4^+$ T-cell line with levels of CCR5 expression similar to primary $CD4^+$ T cells, were electroporated with a CCR5-ZFN expression plasmid encoding the ZFN201 pair to yield an endogenous CCR5 disruption level of 2.4% of the alleles.

This ZFN-treated cell population was then infected with HIV-$1_{BAL}$ or mock infected on day 7, cells were expanded in continuous culture for 70 days, and the proportion of ZFN-modified alleles measured by DNA analysis pre-infection and on days 3, 10, 21, 31, 42 and 52 after infection.

Figure 15:
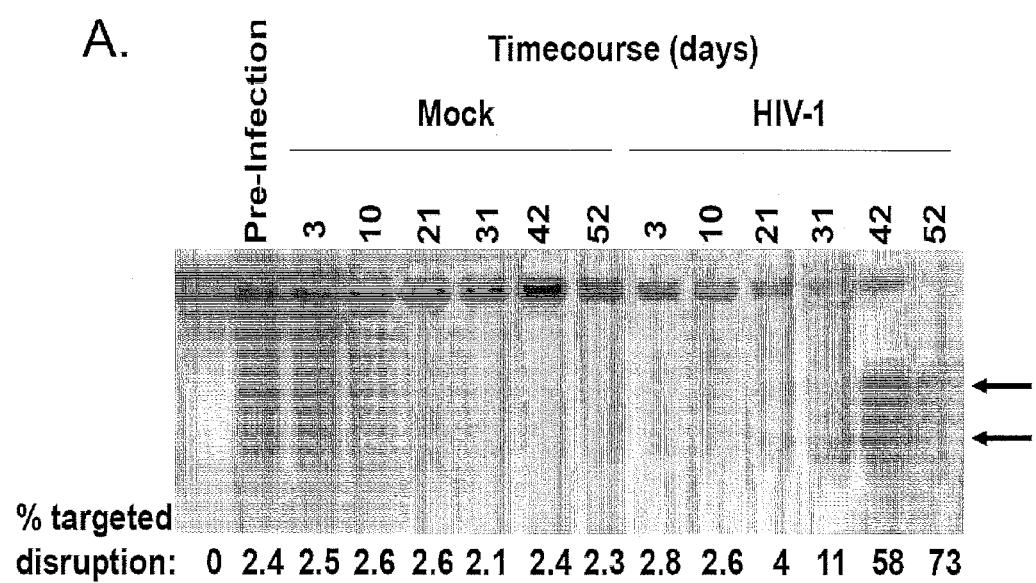
FIG. 15 shows the level of ZFN-disrupted CCR alleles, determined by Cel-1 assay, at days 3, 10, 21, 31, 42 and 52 post-HIV-1 challenge with R5-tropic HIV-1$_{BAL}$ or after mock HIV infection. Cells with disrupted CCR5 alleles remained at stable levels in mock infected cultures, but were enriched in the presence of HIV-1.

As shown in FIG. 15, by day 52 of infection, the HIV-1 infected PM1 culture underwent a ~30-fold enrichment for ZFN-modified CCR5 alleles (~73%). In contrast, the mock infected population showed stable persistence of the ZFN-disrupted CCR5 alleles (~2.3%), indicating no adverse consequences in growth rates for cells carrying a ZFN-modified allele in the absence of selective pressure. PM1 cells electroporated with control (non-CCR5-targeted) ZFN expression plasmids were susceptible to HIV-1 infection and showed no evidence of CCR5 disruption.

These results demonstrate that HIV-1 infection provides a powerful selective advantage for CCR5-ZFN modified cells and that the selective advantage is maintained long-term in culture.

B. ZFN-Mediated Mutations

The molecular identity of the ZFN-mediated mutations in the CCR5 gene in the PM1 cells was also determined by PCR-amplification and sequencing of the targeted region of CCR5 at day 52 post-infection.

Numerous molecularly distinct short deletions and insertions in 78% of sequence reads (63 out of 81 sequences) were observed (FIG. 16), indicating that persistence of modified CCR5 alleles in the presence of HIV did not result from a single rare event.

All of the mutations mapped at or near the ZFN recognition sites, suggesting the permanent modifications of the CCR5 gene sequence resulted from ZFN cleavage and subsequent repair via NHEJ. While a broad range of different deletion and insertion mutations were observed, a specific 5-bp insertion (a duplication of the sequence between the ZFN binding sites which results in introduction of two stop codons immediately downstream of the isoleucine codon at position 56) represented >30% of all modified sequences (FIG. 16).

C. Superinfection

Superinfection experiments were also conducted to confirm that CCR5-ZFN modified PM1 cells remained susceptible to CXCR4-tropic HIV-1 and maintained a selective advantage when re-infected with CCR5-tropic virus.

Briefly, PM1 cells were mock transfected, or transfected with plasmids encoding the CCR5-ZFN 201 pair or a control ZFN pair (GR) as described above. These cell populations were challenged with HIV-1$_{BAL}$ and on day 59 post-infection a portion of each sample was mixed with parental, non-transfected PM1 cells and re-infected with either CXCR4-tropic HIV-1$_{BK132}$ or CCR5-tropic HIV-1$_{BAL}$. These re-infected cultures were followed over time and analyzed for gene disruption frequency on day 21 post-reinfection (day 80 post-initial infection). Cells infected with HIV-1$_{BAL}$ re-enriched for ZFN-modified cells (64%) following dilution with the PM1 cells, whereas in cell populations that were mock infected or infected with the CXCR4-tropic HIV-1$_{BK132}$, little or no selective advantage was observed for CCR5 disrupted cells.

GHOST-CXCR4 cells were also challenged with supernatants (5 µl) from cultures of HIV-1 challenged CCR5-ZFN transfected PM1 cells removed at early (day 3) and late (day 56) time points. These cultures showed no CXCR4-dependent infection. The same supernatants applied to GHOST-CCR5 cells remained infectious, although to a lesser degree, with the exception of the CCR5-ZFN transfected sample suggesting that the >30-fold enrichment for CCR5 null PM1 cells had resulted in greatly reduced viral infectivity by day 56 of the culture. Thus, viral evolution toward CXCR4 co-receptor usage was not detected in supernatants collected at early and late timepoints from CCR5-ZFN treated and HIV-1 infected cultures.

In addition, V3 loop sequences were obtained from supernatants of HIV-1 challenged PM-1 cells transfected with plasmids expressing either CCR5-ZFNs or a GFP control to determine the effects of ZFN generated CCR5 null cell enrichment on viral tropism over time. 150 proviral HIV DNA sequences were isolated from longitudinal culture of HIV-1$_{BAL}$ infected CCR5 ZFN-treated PM-1 cells; of these, 88 were isolated on day 3, and 62 were isolated on day 52 after infection. As a control, 78 HIV DNA sequences were isolated from the HIV infected GFP-treated PM-1 cells; 45 at day 3 and 33 on day 52. The sequences were evaluated for changes in tropism by matching the R5, R5×4, or X4 consensus V3 loop sequences disclosed by Hung et al. (1999) *J. Virol.* 73:8216-8226. All V3 loop sequences from the GFP and CCR5-ZFN treated at both day 3 and day 52 samples most closely matched the CCR5 consensus sequence, suggesting no rapid evolution toward switching co-receptor usage; consistent with the above data showing infectivity in only the CCR5-GHOST reporter cell line.

These results demonstrate that transient expression of CCR5-ZFNs establishes stable and selective resistance to CCR5-tropic HIV-1, similar to that observed in individuals carrying the naturally occurring CCR5Δ32 mutation.

Example 16

In Vitro Selection of CCR5-ZFN Modified Primary Cd4 T Cells

A. Disruption of CCR5 with ZFNs

To determine the efficacy of CCR5-ZFNs in primary human cells, CD4$^+$ T cells from healthy donors with a wild-type CCR5 gene were transduced with Ad5/35 vectors encoding either CCR5-ZFNs 215 or CCR5-ZFNs 224 to provide transient, high efficiency ZFN delivery. Multiplicity of infection (MOI)-dependent levels of ZFN-mediated CCR5 disruption (reaching 40-60% of the CCR5 alleles) were observed in multiple experiments using cells isolated from different donors. An example is shown in FIG. 17.

As shown in FIG. 18, the population-doubling rate of the modified primary CD4 T cells was indistinguishable from that of non-transduced cells, with the proportion of CCR5-modified alleles remaining stable for at least one month during in vitro culture.

B. HIV Challenge

The resistance of bulk ZFN-modified CD4 T cells to HIV infection in vitro was also evaluated.

Individuals carrying the naturally occurring CCR5Δ32 mutation have been shown to be protected from HIV infection and progression. See, for example, Samson et al. (1996) *Nature* 382:722-725 (1996); Huang (1996) *Nat Med.* 2:1240-1243 (1996); Berger et al. (1999) *Annu. Rev. Immunol* 17:657-700. In a control experiment, CD4$^+$ T cells from a donor homozygous for the CCR5Δ32 allele were mixed with CD4$^+$ T cells from a CCR5 wild type donor at the indicated ratios, and challenged with HIV-1$_{BAL}$. Following challenge, an ~2-fold enrichment for CCR5Δ32 CD4 T cells, compared to the parallel mock-infected samples, was observed.

Figure 19:
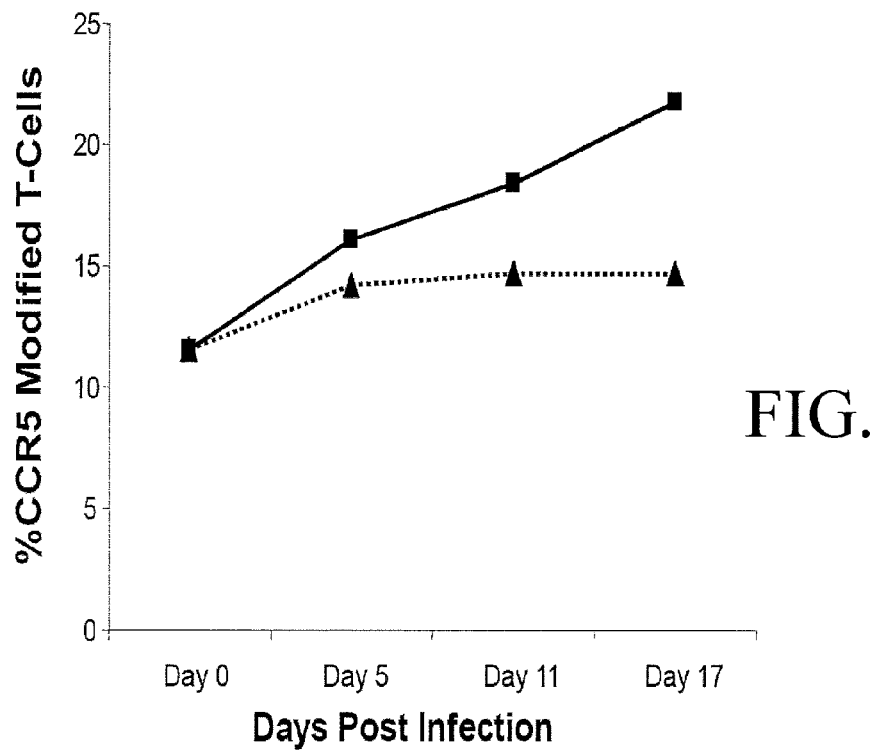
FIG. 19 depicts enrichment of ZFN-disrupted CCR5 alleles in ZFN 215-transduced CD4⁺ T cells over time following in vitro challenge with CCR5-tropic HIV-1$_{US1}$, compared to mock infected cultures. CCR5 disruption was measured using the Surveyor® nuclease (Cel-1) assay. The line joining squares depicts HIV infected cells and the line joining the triangles depicts mock infected cells. An ~10% starting level of ZFN-disrupted CCR5 alleles was obtained by mixing Ad5/35 transduced CD4 T cells with unmodified CD4 T cells (1:3).

Infection of a bulk CCR5-ZFN transduced CD4$^+$ T cell population with CCR5-tropic HIV-1$_{US1}$ also resulted in a two-fold enrichment of gene-edited cells containing ZFN-disrupted CCR5 alleles (measured using the Surveyor® nuclease (Cel-1) assay as described above) over 17 days of culture, while mock-infected control populations maintained a stable level of ZFN-disrupted CCR5 alleles (FIG. 19). In parallel experiments, CCR5-ZFN transduced cells challenged with HIV-1$_{US1}$ produced significantly lower levels of soluble p24 than controls, consistent with the frequency of CCR5 disruption in the population. CD4 T cells transduced with an Ad5/35 GFP control vector showed no detectable disruption of their CCR5 gene.

Thus, CD4$^+$ T cells made CCR5 null via ZFN transduction were selected with similar efficiency to CD4 T cells homozygous for the naturally occurring CCR5Δ32 allele during HIV-1 infection.

Example 17

Specificity of CCR5-ZFNs in Primary CD4 T Cells

A. Double-Stranded Breaks

To quantify the number of double-stranded breaks (DSBs) generated post-ZFN expression, we conducted intranuclear staining for genome-wide DSBs via immunodetection of P53BP1 foci as an unbiased measure of ZFN action throughout the nucleus. P53BP1 is recruited to the sites of DSBs early in the repair response and is required for NHEJ (Schultz et al. (2000) *J Cell Biol.* 151:1381-1390). Briefly, 24 hours post-transduction of CD4$^+$ T cells with Ad5/35 vectors expressing CCR5 targeted ZFNs, the number of 53BP1 immunoreactive foci per nucleus of the CD4 T cells was determined.

Intranuclear staining for P53BP1 was performed using fixation with methanol or paraformaldehyde followed by nuclear permeabilization with 0.5% Triton. Affinity purified rabbit anti-P53BP1 (Bethel Laboratories) and secondary Alexa Fluor™ 488 F(ab')2 goat anti-rabbit IgG (H+L) antibody was from Invitrogen. Antibodies were used at 2 to 5 µg/ml final concentration. Epifluorescence microscopy was performed using a Zeiss Axioplan-II (Thornwood N.Y.) with a Zeiss 63x PlanApo objective having a numerical aperture of 1.4.

Images were acquired and analyzed using Improvision Volocity™ software package (Lexington Mass.) acquisition and classification modules. Analysis of discrete regions of P53BP1 fluorescence was performed by adjusting exposure time and thresholds to minimize autofluorescence and by intensity gating to include the top 40% of fluorescence. Individual regions identified were then enumerated and measured. Only green fluorescent regions that colocalized with DAPI fluorescence were included in final analyses.

Figure 20:
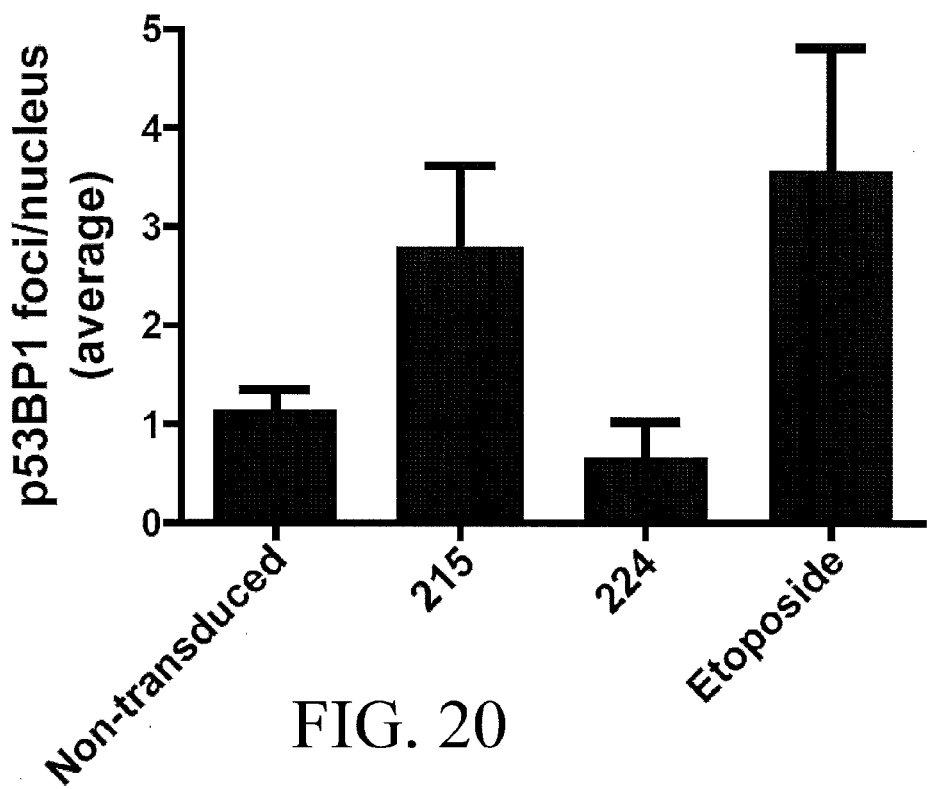
FIG. 20 is a graph depicting average intranuclear P53BP1 immunostaining foci in primary CD4⁺ T Cells, determined 24 hours after transduction with Ad5/35 vectors expressing CCR5 ZFN pairs 215 or 224. Intranuclear foci were counted from a minimum of 100 nuclei per condition using Volocity™ software. Results obtained from positive control cells treated with etoposide and negative control cells (non-transduced) are also shown.

Results are shown in FIG. 20. There was no significant difference in the mean number of intranuclear P53BP1 foci when comparing non-transduced and ZFN 224 transduced CD4 T cells. In contrast, etoposide-treated positive control cells (p=0.004) or cells transduced with an Ad5/35 vector expressing ZFN 215 (p=0.003) showed a statistically significant elevation in P53BP1 intranuclear foci when compared to non-transduced cells. In addition, no significant difference in the mean perimeter of p53BP1 foci was observed among all conditions. DNA analysis confirmed equivalent degrees of cleavage at the intended target site in the CCR5 gene by both ZFN 215 and ZFN 224.

B. Determination of the Consensus ZFN Binding Site

To confirm the specificity of ZFN 224 action, the consensus ZFN binding sites were determined and found to match the unique intended target sequence in CCR5. Binding site preferences for each of the 2 zinc finger proteins comprising ZFN-224 were assayed using a site selection method as follows: (1) first, an HA-tagged version of the ZFP of interest was expressed via the TnT quick coupled transcription-translation system (Promega), and incubated with a pool of partially randomized DNA sequences in the presence of biotinylated anti-HA Fab fragments (Roche) and poly dIdC competitor DNA (Sigma); (2) the protein—along with any productively bound DNA sequences—was captured on streptavidin coated magnetic beads (Dynal); (3) the magnetic beads were placed in Roche PCR master mix containing the appropriate primers and the bound DNA was then released and PCR amplified. This amplified pool of DNA was then used as the starting DNA pool for subsequent rounds of ZFP binding, enrichment and amplification. Cycles comprising steps (1)-(3) were repeated for a total of four rounds of selection. Finally, DNA fragments amplified after the final round were cloned and sequenced. The randomized region of each DNA sequence was aligned to determine the consensus binding site sequence for the zinc finger DNA binding domain. The consensus binding sites determined by this method agreed with the binding sites specified in Table 1.

Target sequence preferences for the two CCR5 ZFNs of the ZFN 224 pair (8196z and 8266, Table 1), determined as described above, were used to guide a genome wide bioinformatic prediction of the top 15 potential off-target, sites in the human genome. This bioinformatic analysis searched for and ranked the potential off-target sites as follows:

All potential DNA binding sites for the two members of the ZFN224 pair (8196z and 8266, Table 1) were identified in the human genome, allowing for up to two base pair mismatches from the consensus sequences of each target site determined as described above.

All possible cleavage locations were identified using the complete list of binding sites (identified as described in the previous paragraph) that allowed any two ZFNs (including homodimerization and heterodimerization events) to bind in the appropriate configuration for nuclease activity (i.e. ZFNs binding on opposite sides of the DNA with either a 5 or 6 bp spacing between them).

The resulting list of potential cleavage sites was then ranked to give priority to those sites with the highest similarity to the consensus for each ZFN as defined by the site selection method described above. Briefly, the site selection data was used to create a probability for the recognition of all four nucleotides (A, C, G or T) in each of the 12 positions of the binding site for each ZFN. Each putative ZFN binding site was scored as the product of these twelve (12) probabilities. (Note that to eliminate a score or probability of zero every position had a single count added for each nucleotide (A, C, G or T) prior to normalization to ensure no entry in the probability table was zero). Similarly, the score for a given off-target cleavage site (requiring two such ZFN sites to be occupied) was calculated as the product of the two scores given to each of the two ZFN binding sites comprising the putative cleavage site. Of the 15 sites identified, 7 fall within annotated genes and 2 of these fall within exonic sequence. These seven genes share the following characteristics; (i) their mutation or disruption has not been connected with any known pathology; and (ii) with the exception of CCR2, they have no described function in CD4 T-cells.

Surveyor™ nuclease assays revealed no detectable ZFN activity (1% limit of detection) at any of these sites with the exception of CCR2 (the closest relative of the CCR5 gene in the human genome). We observed 4.1% modification of CCR2 alleles in the population under conditions that revealed 35.6% ZFN-modified CCR5 alleles. However, loss of CCR2 in CD4 T cells should be well tolerated since CCR2−/− mice display numerous mild phenotypes predominantly associated with delayed macrophage trafficking and recruitment (Peters et al. (2000) *J. Immunol.* 165:7072-7077). Mutant alleles of CCR2 have been correlated with delayed progression to AIDS in HIV infected individuals, although no influence on the incidence of HIV-1 infection was observed (Smith et al. (1997) *Nat. Med.* 3:1052-1053). Thus, parallel mutation of CCR2 is unlikely to be deleterious and may increase protection of modified CD4 T cells to HIV infection.

The combination of ZFP consensus binding site-directed analysis of the most similar off-target sites in the genome with the unbiased intranuclear staining for genome-wide DSB generation indicates that ZFN 224 is a highly specific engineered nuclease with measurable activity only at the CCR5 gene and, to a ~10-fold lesser extent, at the CCR5 homologue CCR2.

Example 18

In Vivo Selection of CCR5-ZFN Modified Primary CD4 T Cells

A NOG/SCID mouse model of HIV infection was used to test adoptive transfer and protection from HIV infection of the ZFN-modified CD4 T cells in vivo. See Schultz et al. (2007) *Nat. Rev. Immunol.* 7:118.

Primary CD4 T cells were transduced with the Ad5/35 vectors and expanded in culture using anti-CD3/anti-CD28 coated magnetic beads in the presence of IL-2. NOG/SCID mice (7-9 weeks old) were randomly assigned to 2 treatment groups (n=8 mice per group) with equal mix of males and females in each group. These mice were maintained in a defined flora animal facility. Both groups received an IP injection of 100 µl of PBS containing 7.5 million CCR5-ZFN ex-vivo expanded primary human CD4 T cells and 1 million resting, autologous PBMCs to promote engraftment in combination. In addition, the mock treated animals received 1 million non-infected PHA-activated autologous PBMCs, whereas the infected group of animals received 1 million CCR5-tropic HIV-1$_{US1}$ infected PHA-activated PBMCs.

To assess engraftment, peripheral blood sampling was performed three and four weeks after adoptive transfer and analyzed for engraftment by flow cytometry for human CD45, CD4 and CD8. After 4.5 weeks, mice were sacrificed and splenic CD4 T lymphocytes were purified using Miltenyi MACS separation kit. Only samples with greater than 75% purity were used for the final analysis. To determine CCR5 disruption frequency, a modified Surveyor™ nuclease assay was employed by utilizing a nested PCR approach to fully remove contaminating mouse genomic DNA. The DNA from purified splenic CD4 cells was amplified first using 50 pmols of outside primers (R5-det-out-F1: CTGCCTCATAAGGT-TGCCCTAAG (SEQ ID NO:31); C5_HDR_R: CCAG-CAATAGATGATCCAACTCAAATTCC (SEQ ID NO:32)) for 25 cycles (95° C.—30 sec., 58° C.—30 sec., and 68° C.—3 min.), the resulting material was gel purified, and the Surveyor™ nuclease assay was performed on the purified product as per the manufacturers' recommendations.

After a month of HIV infection in vivo, mice were sacrificed and genomic DNA from human CD4 T lymphocytes purified from the spleen was used for analysis of ZFN-mediated CCR5 disruption, using the Surveyor™ nuclease assay described above. Samples from 2 mice (one HIV-infected and one mock-infected) were excluded from analysis due to inadequate CD4 cell purification:

All groups showed equal engraftment, although the HIV infected groups exhibited a reduced CD4 to CD8 T cell ratio, consistent with HIV-induced CD4 T cell depletion.

Figure 21:
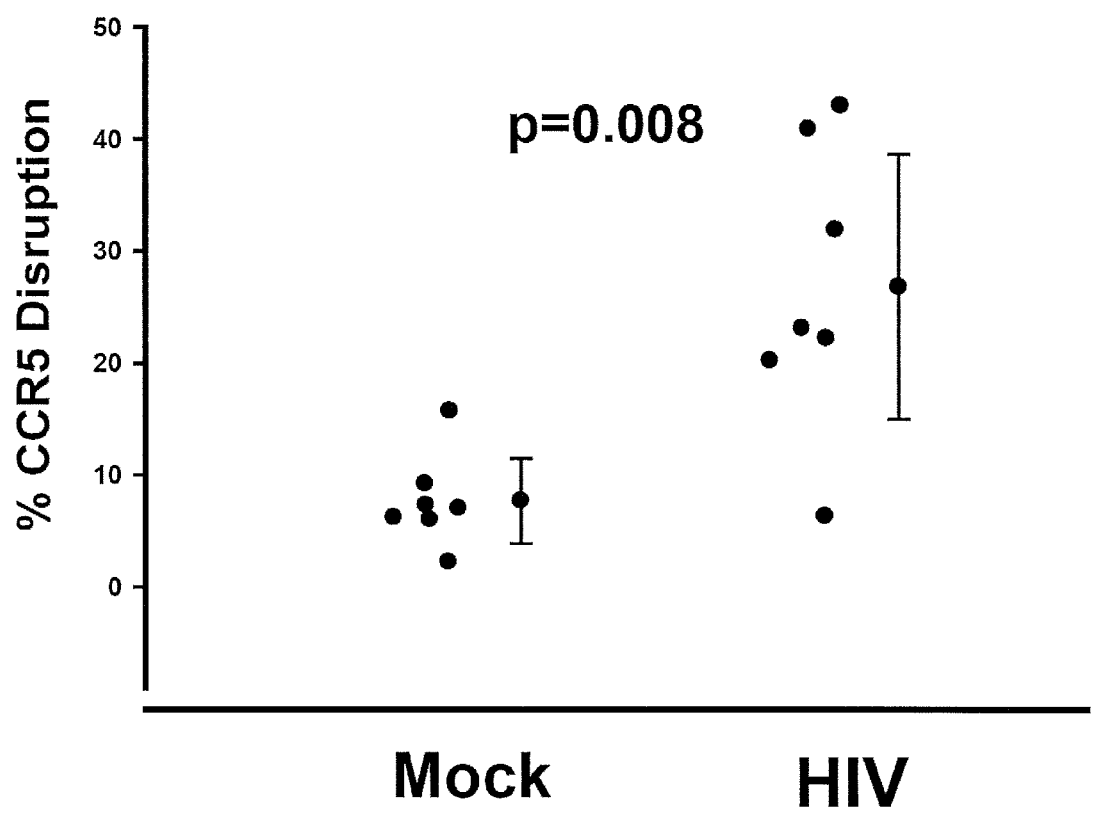
FIG. 21 is a graph depicting in vivo CCR5 disruption frequencies, measured using the Surveyor® nuclease (Cel-1) assay, in CD4 cells isolated on day 40 from the spleens of control (mock infected) or HIV-infected mice. Results for each group were averaged and analyzed using an unpaired T-test.

Further, FIG. 21 shows that an approximately 3-fold enrichment for ZFN-disrupted CCR5 alleles was observed in the HIV infected group (27.5% average CCR5-disruption), compared to animals receiving an identical starting population of ZFN-treated CD4 T cells in the absence of HIV infection (mock group, 8.5% average CCR5 disruption, p=0.008).

These data demonstrate (i) a selective advantage for ZFN-transduced primary human CD4+ T cells in the presence of HIV-1 in vivo, and (ii) normal engraftment and growth of these same ZFN-transduced cells even in the absence of this selective pressure. These data indicate that the transient delivery of engineered ZFNs succeeded in reproducing the CCR5Δ32 null genotype (and resulting phenotypes).

Thus, ZFNs as described herein cleave specifically in the CCR5 gene, and cause permanent disruption of greater than 50% of the CCR5 alleles in a bulk population of primary human CD4+ T-cells. In addition, the genetic disruption of CCR5 by ZFNs provides robust, stable, and heritable protection against HIV-1 infection in vitro and in vivo. ZFN-modified CD4 T-cells engraft and proliferate normally upon stimulation.

What is claimed is:

1. A protein comprising an engineered zinc finger protein DNA-binding domain, wherein the DNA-binding domain comprises four zinc finger recognition regions ordered F1 to F4 from N-terminus to C-terminus, and wherein F2, F3, and F4 comprise the following amino acid sequences:

F2: QKINLQV (SEQ ID NO: 17)

F3: RSDVLSE (SEQ ID NO: 12)

F4: QRNHRTT. (SEQ ID NO: 13)

2. The protein according to claim 1, wherein F1 comprises the amino acid sequence RSDNLGV (SEQ ID NO:16).

3. The protein according to claim 1, wherein F1 comprises the amino acid sequence RSDNLSV (SEQ ID NO:10).

4. A protein according to claim 1, further comprising a cleavage domain.

5. The protein of claim 4, wherein the cleavage domain is a cleavage half-domain 6. The protein of claim 5, wherein the cleavage half-domain is a wild-type FokI cleavage half-domain.

7. The protein of claim 5, wherein the cleavage half-domain is an engineered FokI cleavage half-domain.

8. A polynucleotide encoding the protein of claim 1.

9. A gene delivery vector comprising a polynucleotide according to claim 8.

10. The gene delivery vector of claim 9, wherein the vector is an adenovirus vector.

11. The gene delivery vector of claim 8, wherein the adenovirus vector is an Ad5/35 vector.

12. An isolated cell comprising the protein of claim 1.

13. The isolated cell of claim 12, further comprising a protein comprising an engineered zinc finger protein DNA-binding domain, wherein the DNA-binding domain comprises four zinc finger recognition regions ordered F1 to F4 from N-terminus to C-terminus, and wherein F1, F3, and F4 comprise the following amino acid sequences:

F1: DRSNLSR (SEQ ID NO: 2)

F3: RSDNLAR (SEQ ID NO: 4)

F4: TSGNLTR. (SEQ ID NO: 8)

14. An isolated cell comprising the polynucleotide of claim 8.

15. The isolated cell of claim 14, further comprising a polynucleotide encoding a protein comprising an engineered zinc finger protein DNA-binding domain, wherein the DNA-binding domain comprises four zinc finger recognition regions ordered F1 to F4 from N-terminus to C-terminus, and wherein F1, F3, and F4 comprise the following amino acid sequences:

F1: DRSNLSR (SEQ ID NO: 2)

F3: RSDNLAR (SEQ ID NO: 4)

F4: TSGNLTR. (SEQ ID NO: 8)

16. The cell of claim 12, wherein the cell is selected from the group consisting of a hematopoietic stem cell, a T-cell, a macrophage, a dendritic cell and an antigen-presenting cell.

17. The cell of claim 16, wherein the T-cell is a CD4$^+$ cell.

18. The cell of claim 14, wherein the cell is selected from the group consisting of a hematopoietic stem cell, a T-cell, a macrophage, a dendritic cell and an antigen-presenting cell.

19. The cell of claim 18, wherein the T-cell is a CD4$^+$ cell.

20. A method for inactivating the CCR-5 gene in a human cell, the method comprising administering to the cell a polynucleotide according to claim 8.

21. The method of claim 20, further comprising administering a polynucleotide encoding a protein comprising an engineered zinc finger protein DNA-binding domain, wherein the DNA-binding domain comprises four zinc finger recognition regions ordered F1 to F4 from N-terminus to C-terminus, and wherein F1, F3, and F4 comprise the following amino acid sequences:

```
                        (SEQ ID NO: 2)
    F1: DRSNLSR (SEQ ID NO: 4)
    F3: RSDNLAR (SEQ ID NO: 8)
    F4: TSGNLTR.
```

22. The method of claim 20, wherein the cell is selected from the group consisting of a hematopoietic stem cell, a T-cell, a macrophage, a dendritic cell and an antigen-presenting cell.

23. The method of claim 22, wherein the T-cell is a $CD4^+$ cell.

* * * * *